United States Patent [19]

Rogers et al.

[11] Patent Number: 4,642,338

[45] Date of Patent: Feb. 10, 1987

[54] FLUOROPHENOXYPHENOXYPROPION-ATES AND DERIVATIVES THEREOF

[75] Inventors: Richard B. Rogers, Midland, Mich.; B. Clifford Gerwick, III, Clayton, Calif.

[73] Assignee: The Dow Chemical Company, Midland, Mich.

[21] Appl. No.: 709,142

[22] Filed: Mar. 7, 1985

Related U.S. Application Data

[63] Continuation-in-part of Ser. No. 528,711, Sep. 1, 1983, Pat. No. 4,550,192.

[51] Int. Cl.[4] ............................................. C07C 101/72
[52] U.S. Cl. ..................... 534/558; 560/47; 560/45; 71/121; 71/108; 71/109
[58] Field of Search ................ 71/127, 108, 109; 568/637; 534/558; 560/45

[56] References Cited

U.S. PATENT DOCUMENTS

| | | | |
|---|---|---|---|
| 3,966,826 | 6/1976 | Tröshen | 568/637 |
| 4,355,186 | 10/1982 | Becker et al. | 568/52 |
| 4,388,472 | 1/1983 | Cartwright | 71/108 |

FOREIGN PATENT DOCUMENTS

| | | | |
|---|---|---|---|
| 873844 | 5/1979 | Belgium . | |
| 2601548 | 7/1977 | Fed. Rep. of Germany | 69/67 |
| 2758304 | 7/1979 | Fed. Rep. of Germany | 29/36 |
| 2905458 | 8/1979 | Fed. Rep. of Germany | 69/73 |
| 3004695 | 8/1981 | Fed. Rep. of Germany | 568/637 |
| 46-13593 | 1/1971 | Japan | 71/121 |
| 2042503 | 9/1980 | United Kingdom | 59/13 |

*Primary Examiner*—Paul J. Killos
*Attorney, Agent, or Firm*—Joseph T. Majka; Ronald G. Brookens

[57] ABSTRACT

Novel intermediates useful in the preparation of fluorophenoxyphenoxypropionates and derivatives thereof which possess herbicidal activity selectively in the presence of broadleaf crops.

6 Claims, No Drawings

FLUOROPHENOXYPHENOXYPROPIONATES AND DERIVATIVES THEREOF

CROSS REFERENCE TO RELATED APPLICATION

This application is a continuation-in-part of Ser. No. 528,711 filed Sept. 1, 1983 and now U.S. Pat. No. 4,550,192.

BACKGROUND OF THE INVENTION

The present invention relates to novel fluorophenoxyphenoxypropionates and derivatives thereof which are useful as herbicides. The present invention also relates to herbicidal compositions containing these novel compounds; to methods of using these compounds for the control of weeds in non-crop areas as well as in the presence of valuable crops; and to novel intermediates used to make these compounds.

Various 4-phenoxy-phenoxy-propionic acids are known as herbicidal agents. U.S. Pat. No. 4,332,961 discloses 2-[4-(4-trifluoromethylphenoxy)phenoxy]alkane carboxylic acid and derivatives thereof wherein the "4-trifluoromethylphenoxy group" may optionally contain a chloro substituent. U.S. Pat. No. 4,332,960 discloses 2-[4-(2-hydrogen or halogen-4-trifluoromethyl-phenoxy)-phenoxy]propionic acid and derivatives thereof wherein hydrogen is the preferred substituent at the 2' position. Both of these patents teach the compounds disclosed in them as possessing herbicidal activity.

U.S. Pat. No. 4,370,489 discloses 2-[4-(2-chloro-4-bromo-phenoxy)-phenoxy]propionic acid and derivatives thereof as possessing herbicidal activity.

Heretofore, 2-[4-(2-fluoro-4-substituted-phenoxy)-phenoxy]propionic acids and agriculturally acceptable derivatives thereof have not been disclosed.

SUMMARY OF THE INVENTION

The present invention is directed to fluorophenoxyphenoxypropionates of the formula (I):

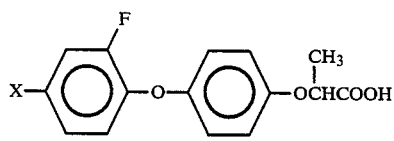

(I)

wherein

X represents —Cl, —CF$_3$, —I, —Br, F, —OCF$_3$, —CF$_2$Cl, —CF$_2$H or —OCF$_2$CCl$_2$H, and agriculturally acceptable derivatives (salts, amides and esters) thereof.

The compounds of the above Formula I, hereinafter referred to as "active ingredients", have been found to be active as herbicides in the presence of broadleaf crops and are unexpectedly superior in activity compared to compounds known in the art. Additionally, compounds of Formula (I), above, wherein X is —Cl and particularly wherein X is —Br, are surprisingly selective to small grain crops, such as wheat and barley, i.e., substantially non-phytotoxic to small grain crops. Accordingly, the present invention also encompasses herbicidal compositions containing one or more active ingredients as well as methods of controlling unwanted vegetation in such crops. Such methods comprise, for example, applying a herbicidally effective amount of one or more active ingredients preemergently or postemergently to the locus of the undesired vegetation, and particularly to the locus where a valuable crop is to germinate and grow.

DETAILED DESCRIPTION OF THE INVENTION

The term "herbicide" is used herein to mean an active ingredient which controls or adversely modifies the growth of plants. By "growth controlling" or "herbicidally-effective" amount is meant an amount of active ingredient which causes an adversely modifying effect and includes deviations from natural development, killing, regulation, dessication, retardation, and the like.

The term "plants", when used herein, is meant to include germinant seeds and emerging seedlings as well as established vegetation.

The term "halogen" when used herein is meant to include F, Cl, I and Br.

The term "agriculturally acceptable salts, amides and esters", when used to describe the active ingredients disclosed herein, is meant to encompass any salt, amide, ester or derivative of said active ingredients (acids) which (1) does not substantially affect the herbicidal activity of said active ingredients, or (2) is or can be hydrolyzed and/or oxidized in plants or soil to a carboxyl moiety that is in undissociated and/or dissociated form.

Agriculturally acceptable derivatives of the active ingredients include compounds of the formula:

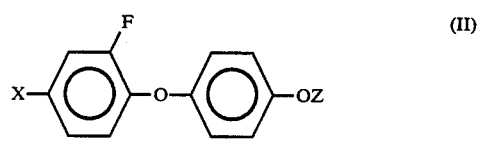

(II)

wherein

X represents —Cl, —CF$_3$, —I, —Br, F, —OCF$_3$, —CF$_2$Cl, —CF$_2$H or —OCF$_2$CCl$_2$H; and Z represents an organic moiety containing N, O or S atoms, a metallic cation, an ammonium cation, or an organic amine cation and is or can be hydrolyzed and/or oxidized in plants or soil to a carboxyl moiety that is in undissociated and/or dissociated form.

Z moieties include, but are not limited to

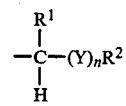

wherein

Y represents a saturated or unsaturated alkyl group containing an even number of carbon atoms, preferably from 2 to 18 carbon atoms;

n represents 0 or 1;

R$^1$ represents H or a C$_1$-C$_3$ alkyl group; and

R$^2$ represents moieties corresponding to one of the following formulae:

-continued

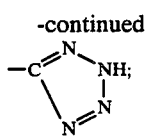 (2)

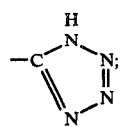 (3)

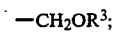 (4)
—C—Hal, wherein Hal is halogen;

 (5)

wherein M represents a metallic cation, ammonium cation or an organic amine cation, typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl;

—CH$_2$OR$^3$; (6)

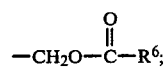 (7)

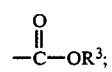 (8)

 (9)

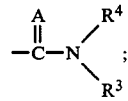 (10)

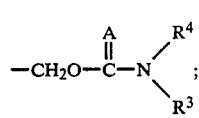 (11)

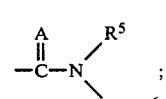 (12)

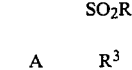 (13)

 (14)

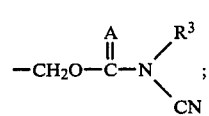 (15)

-continued

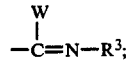 (16)

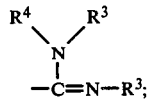 (17)

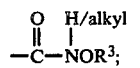 (18)

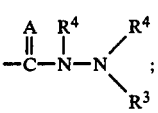 (19)

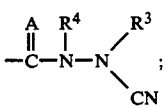 (20)

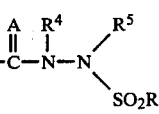 (21)

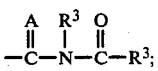 (22)

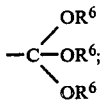 (23)

—C(SR$^6$)$_3$; (24)

 (25)

 (26)

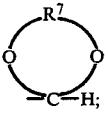 (27)

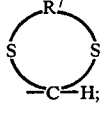 (28)

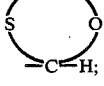 (29)

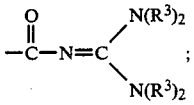 (30)

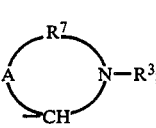 (31)

wherein
W represents —OR$^6$, —SR$^6$ or halogen;
A represents O or S;
R$^3$ represents H or R$^6$;
R$^4$ represents H, alkoxy or R$^6$;
R$^5$ represents H, a metallic cation or R$^6$; and
R$^6$ represents an alkyl (saturated or unsaturated), alicyclic, heterocyclic or aromatic group, unsubstituted or substituted with various other groups not limited to, but including, halo, cyano, nitro and unsubstituted or substituted thio, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl;

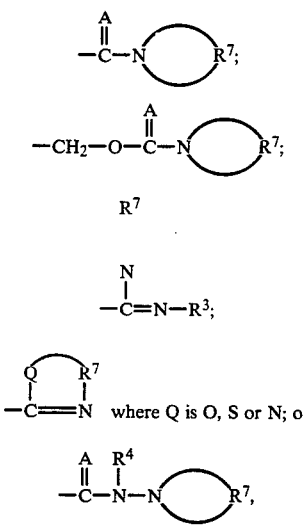

where R$^7$ completes an unsubstituted or substituted heterocyclic ring system and A represents O or S.

R$^2$ is preferably a carboxylic acid group, an alkali or alkaline earth metal salt thereof, an ammonium or organic amine salt thereof or a lower alkyl ester thereof, wherein "lower alkyl" includes straight, branched or cyclic saturated or unsaturated alkyl groups containing no more than 8 carbon atoms. Preferably, n is 0 and R$^1$ is methyl.

In Formula (II) above, the aliphatic groups preferably contain 1 to 8 carbon atoms, the alkenyl and alkynyl groups preferably contain 2 to 8 carbon atoms, the alicyclic groups preferably contain 3 to 8 carbon atoms and the aromatic moiety is preferably phenyl, although other ring systems, including heterocyclic ring systems, may be employed if desired.

In Formula (II) above, X is preferably CF$_3$, Br or Cl and most preferably X is Br. The most preferred compounds are those in which X is Br and Z is

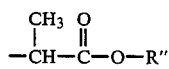

wherein R'' is hydrogen, C$_1$-C$_8$ alkyl, e.g., methyl, ethyl, propyl, isopropyl, isobutyl, n-butyl or n-octyl, or meth-oxypropyl.

The phenoxyphenoxy compounds of Formula (II), also referred to "active ingredients", above are prepared employing procedures analogous to well known procedures for preparing known phenoxyphenoxyalkanecarboxylic acids and derivatives thereof as described in the known art. For example, some of the compounds of Formula (II) above are prepared by reacting an appropriately substituted 1,2-difluorobenzene with an alkali or alkaline earth metal salt of an appropriate hydroxyphenoxy compound in a suitable solvent medium, such as dimethylsulfoxide (DMSO), dimethylformamide (DMF), N-methylpyrrolidone, hexamethylphosphoramide, tetrahydrofuran (THF), or acetonitrile. The reaction is advantageously carried out at an elevated temperature of from 65° C. to 220° C. This reaction can be characterized as follows:

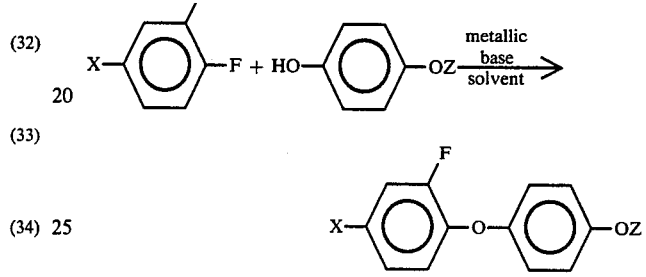

wherein X and Z are as hereinbefore defined. This reaction is preferred when preparing compounds of Formula II wherein X is CF$_3$ or —NO$_2$.

Compounds of Formula (II) above wherein X is —Cl or —Br are preferably prepared by reacting an alkali or alkaline earth metal salt of 4-(4-chloro- or bromo-2-fluorophenoxy)phenol with an halo-Z compound, wherein Z is as defined in Formula (II), in a suitable solvent medium, such as, DMSO, DMF, THF, N-methylpyrrolidone, hexamethylphosphoramide, or acetonitrile. This reaction is advantageously carried out at an elevated temperature of from 40° C. to 220° C. This reaction can be characterized as follows:

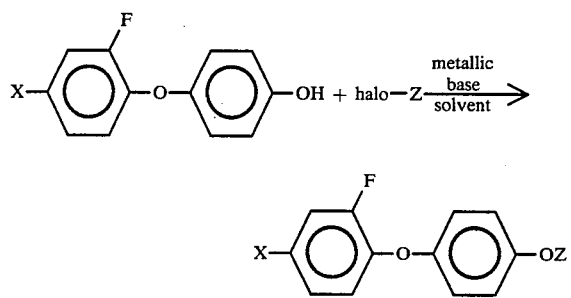

wherein X is Cl or Br, Z is as hereinbefore defined and the metallic base is a base, such as, for example Na$_2$CO$_3$ or K$_2$CO$_3$. However, organic bases such as triethylamine can also be used.

4-(4-(substituted)-2-fluorophenoxy)phenol and salts thereof are novel intermediate compounds and are within the scope of the present invention. These intermediates can be prepared by hydrogenating 4-(4-substituted-2-fluorophenoxy)nitrobenzene with hydrogen in the presence of a Raney nickel catalyst. This reaction can be characterized as follows:

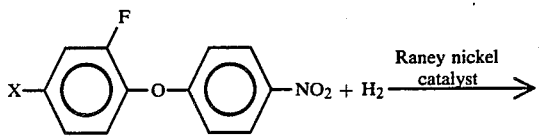

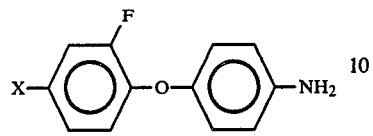

wherein X is as defined hereinbefore. 4-(2-Fluoro-4-(substituted)phenoxy)benzeneamine, also a novel compound and contemplated by the present invention, is reacted with fluoboric acid (HBF₄), sodium nitrite and water to form the tetrafluoroborate salt of 4-(-4-(substituted)-2-fluorophenoxy)benzenediazonium. This reaction can be characterized as follows:

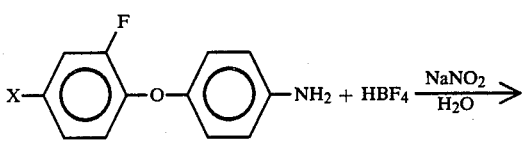

4-(2-fluoro-4-substituted phenoxy)benzenediazonium tetrafluoroborate, another novel compound and contemplated by the present invention, is reacted with (a) aqueous sulfuric acid with heat or (b) an alkali metal trifluoroacetate in trifluoroacetate and water in accordance with the procedure taught in D. E. Horning et al., *Can. J. Chem.*, 51, 2347, (1973), resulting in the formation of 4-(2-fluoro-4-substituted phenoxy)phenol. These reactions can be characterized as follows:

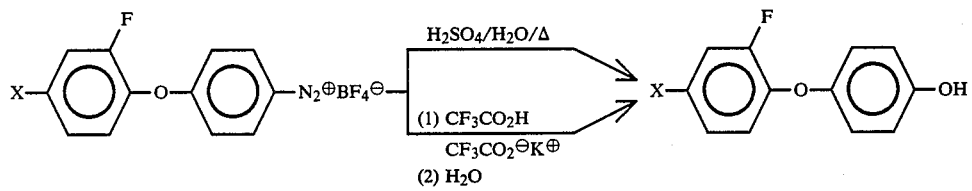

Preferred compounds of the present invention are the compounds of Formula (I) above wherein X represents —CF₃, —Br or —Cl, i.e., 4-(2-fluoro-4-(chloro, bromo or trifluoromethyl)phenoxy)phenoxy propionic acid and agriculturally acceptable derivatives thereof. These preferred compounds are prepared by reacting the appropriate starting materials employing the procedures set forth above. The 4'-trifluoromethyl-2'-fluorophenoxyphenoxy propionates are prepared by reacting 1,2-difluoro-4-trifluoromethylbenzene with a salt of 4-hydroxyphenoxypropionic acid or a derivative thereof, i.e., an ester, or amide derivative of the 4-hydroxyphenoxypropionic acid. This reaction can be characterized as follows:

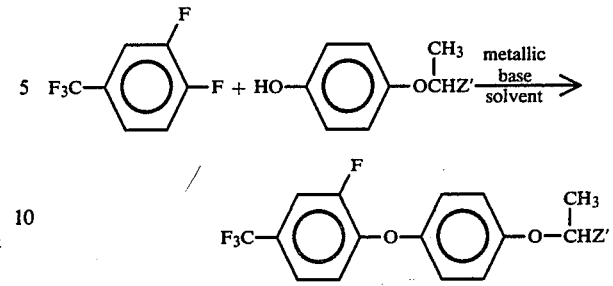

wherein

Z' represents —CO₂H (the acids), —CO₂M', —CO₂R⁸, —COSR⁸, —CONR⁹₂, —CSNH₂, —CN, —CH₂OR⁹ or —CH₂O₂CR⁹;

M' represents Li, Na, K, Mg, Ba or Ca, and corresponds to the cation of the metallic base, or N(R¹⁰)₄;

R⁸ represents C₁–C₈ alkyl, C₃–C₆ cycloalkyl, C₂–C₈ alkenyl, alkynyl, or alkoxyalkyl;

each R⁹ independently represents H or C₁–C₄ alkyl; and

R¹⁰ independently represents H, C₁–C₄ alkyl or C₂–C₃ hydroxyalkyl.

The 4'-chloro-2'-fluorophenoxyphenoxy propionates are prepared by reacting a 4-(4-chloro-2-fluorophenoxy)phenol with a halopropionate in the presence of a base and solvent as described above. This reaction can be characterized as follows:

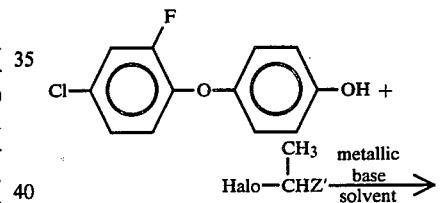

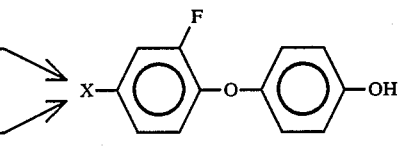

wherein Z' is as defined above.

The 4'-bromo-2'-fluorophenoxyphenoxy propionates are prepared by reacting a 4-(4-bromo-2-fluorophenoxy)-phenol with a halopropionate in the presence of a base and solvent as described above. This reaction can be characterized as follows:

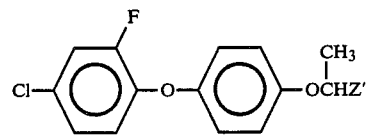

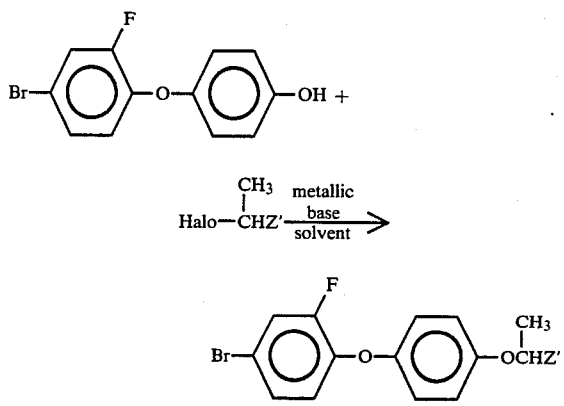

wherein Z' is as defined above.

Alternatively the 2-(4-(4-halo-2-fluorophenoxy)-phenoxy)propionates can be prepared by diazotizing a compound of the following formula

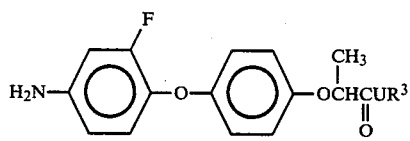

where U=O,N and $R^3$ is as previously defined, and decomposing the diazonium salts using standard techniques to give the desired halogenated derivatives as illustrated in some of the following examples.

The terms "$C_1$–$C_4$ alkyl" and "$C_1$–$C_8$ alkyl" refer to different size alkyl groups which may be straight, branched, or cyclic, when the group contains at least three carbon atoms, and, contain 1∝4 or 1–8 carbon atoms respectively. The terms "$C_2$–$C_3$ hydroxyalkyl" and "$C_3$–$C_6$ hydroxyalkyl" refer to different size hydroxyalkyl groups having 2–3 or 3–6 carbon atoms, respectively, and the alkyl portion may be straight or branched, or cyclic when the group contains at least three carbon atoms.

Once prepared, the compounds of the present invention are recovered employing standard, well-known extraction and purification techniques, such as, for example, solvent extraction with ether.

The following examples further illustrate the present invention. No attempt has been made to balance any equations described herein.

EXAMPLE 1:

Preparation of 2-[4-(2-fluoro-4-trifluoromethylphenoxy)phenoxy]propionic acid methyl ester

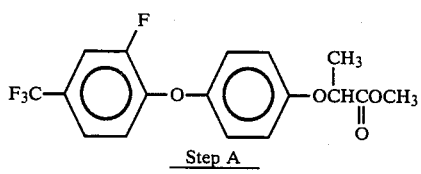

Step A

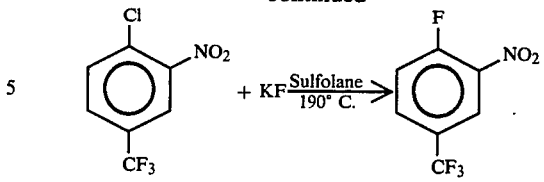

A stirred mixture of potassium fluoride (58 grams (g), 1 mol) and potassium carbonate (2 g) in sulfolane (300 ml) was subjected to vacuum distillation until 75 ml of liquid had distilled. This effectively removes any moisture from the system. The distillation head was removed and 4-chloro-3-nitrobenzotrifluoride (95 g, 0.42 mol) was added. The resulting mixture was heated at 190° C. for two hours, then allowed to cool to approximately 100° C. A 6 inch Vigreaux column was added to the reaction flask, and the product rapidly distilled under vacuum (~1 mm). The light yellow liquid so obtained was mostly the desired 4-fluoro-3-nitrobenzotrifluoride but contained small amounts of sulfolane (~4 percent) and starting material. This liquid was dissolved in pentane (600 ml), washed with water (3×500 ml), then dried (MgSO$_4$). Removal of the solvent and distillation of the yellow residual liquid gave 59 g (67 percent) of the desired product which had a boiling point (b.p.) of 51° C. at ~1 mm. The nuclear magnetic resonance (NMR) (CDCl$_3$) spectra was consistent with the assigned structure.

Step B

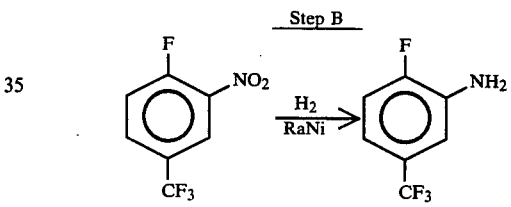

A mixture of 4-fluoro-3-nitrobenzotrifluoride (59 g, 0.282 mol) and Raney Nickel (RaNi) (Aldrich, 5-spoonula scoops) in ethanol (350 ml) was hydrogenated on a Paar apparatus (starting pressure=50 psi) until the theoretical amount of hydrogen had been consumed (~7 hours). The catalyst was filtered off (celite) and the ethanol was carefully evaporated on the rotary evaporator (some product is lost in this process). The residue was distilled to give 39 g (77 percent) of the desired aniline as a nearly colorless liquid which quickly turns yellow on standing. The product had a b.p. of 41° C. at ~1 mm. The NMR (CDCl$_3$) spectra was consistent with the assigned structure.

Step C

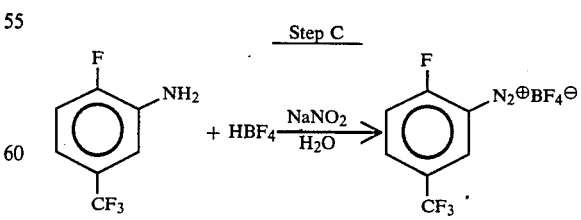

A mechanically stirred solution of 3-amino-4-fluorobenzotrifluoride (17.9 g, 0.1 mol) in 48 percent fluoboric acid (72 g ~0.4 mol of HBF$_4$) and water (100 ml) was cooled to ≦5° C. in an ice-salt bath. To this solution was slowly dropped a solution of sodium nitrite (7.25 g, 0.105 mol) in water (10 ml). Soon after the addition began, a solid began to separate. After about one-quarter of the sodium nitrite solution had been added, the reaction mixture had become very thick. It was necessary to stir very vigorously with an efficient stirrer in order to complete the reaction. After the addition was complete, stirring at $\leq 5°$ C. was continued for an hour, then the solid diazonium salt collected by filtration (medium porosity funnel). The salt was washed with cold 5 percent $HBF_4$ solution (75 ml), then with several portions of cold ether. This material was then dried overnight in a vacuum oven over $P_2O_5$ at 60° C. to give 22 g (79 percent) of the diazonium tetrafluoroborate (shown above) as an off-white solid. The NMR (d6-acetone) spectra was consistent with the assigned structure.

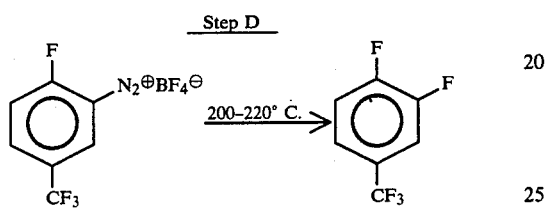

The diazonium salt (22 g) from Step E, which is shown above, was placed in a round-bottom flask (250 ml) equipped with a Dean-Stark trap and a condenser through which ice-water was circulated. The top of the condenser was connected to a trap containing 10 percent NaOH solution. The flask was immersed in an oil bath heated to 200°–220° C. The salt melted, turned dark and decomposed slowly, at first, then decomposed much more vigorously. The decomposition was accompanied by large amounts of gas and smoke. The desired 3,4-difluoro-benzotrifluoride which distilled was collected in the Dean-Stark trap as a dark red liquid (6 g). This was taken up in pentane (20 ml) which was then stirred with $MgSO_4$ and $Na_2CO_3$, filtered and distilled to give pure 3,4-difluorobenzotrifluoride (3.25 g, 22.5 percent) as a colorless liquid having a b.p. of 104° C.

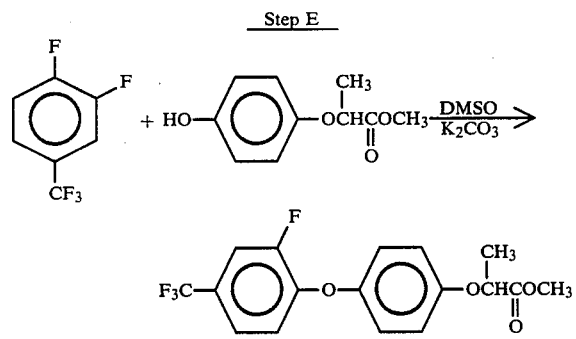

A stirred mixture of 3,4-difluorobenzotrifluoride (1.82 g, 0.01 mol), methyl 2-(4-hydroxyphenoxy)propionate (2.72 g, 0.01 mol) and potassium carbonate (1.5 g) in DMSO (20 ml) was heated at 100°–110° C. for 90 minutes. After cooling, the mixture was poured into water (200 ml), then extracted with ether (2×100 ml). Pentane (50 ml) was added to the ether extracts, and this was washed with water (200 ml). After drying ($MgSO_4$) the solvent was evaporated to give the desired phenoxyphenoxypropionate (2.0 g, 55.9 percent) shown above as a pale yellow oil with a refractive index (RI) of 1.4998 at 25° C. The NMR ($CDCl_3$) spectra for $^1H$ and $^{19}F$ were consistent with the assigned structure.

EXAMPLE 2

Preparation of 2-[4-(4-chloro-2-fluorophenoxy)phenoxy]propionic acid methyl ester

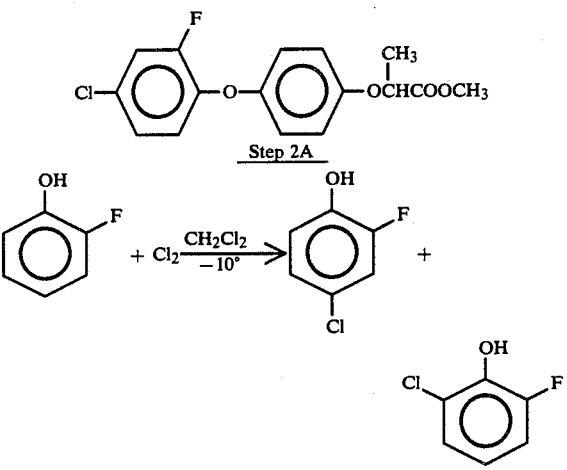

A stirred solution of 2-fluorophenol (20 g; 0.178 mol) in methylene chloride (200 ml) was cooled to −10° C. in an ice-salt bath. Precondensed chlorine (12.62 g; 0.178 mol) was then slowly bubbled into the solution at such a rate that the temperature did not rise above −10° C. After all of the chlorine had been added, and the green color dissipated, the reaction was checked by gas chromatography (g.c.). Even though no chlorine remained, g.c. showed that besides the two chlorinated products, a fair amount (~25%) of the starting phenol remained. At this point there was little or no dichlorinated material present. Additional chlorine was bubbled into the reaction mixture until g.c. showed that all of the starting material had been consumed. At this point, the reaction mixture contained 3% of a dichlorinated material as well as an 8:2 mixture of monochlorinated products. The mixture was poured into water (300 ml) containing excess sodium bisulfite. The organic layer was separated, dried ($MgSO_4$) and the solvent evaporated to give 25.5 g of a light yellow liquid. Fluorine NMR ($CDCl_3$) showed that an 8:2 mixture of monochlorinated products to be present. It was presumed that the major isomer was the desired 4-chloro-2-fluorophenol and that this would react faster in nucleophillic substitution reactions than the more sterically hindered 2-chloro-6-fluorophenol. This mixture was used directly in the next reaction (Step 2B).

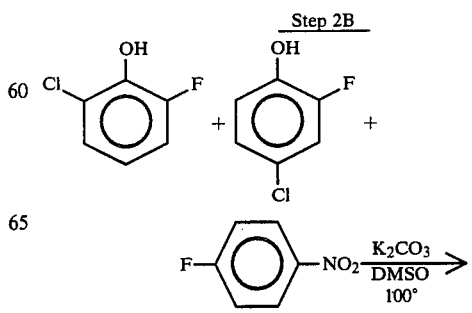

-continued
Step 2B

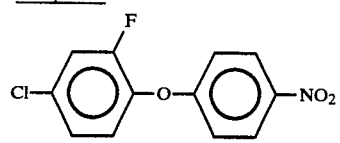

To a stirred mixture of potassium carbonate (25.04 g; 0.18 mol) in DMSO (200 ml) under an argon atmosphere was added an 8:2 mixture (25 g; 0.171 mol) (from Step 2A) of 4-chloro-2-fluorophenol (~20 g; 0.136 mol) and 2-chloro-6-fluorophenol (~5 g; 0.034 mol). To this mixture was added 4-fluoronitrobenzene (18.05 g; 0.128 mol) and the resulting mixture stirred at 100° C. for 30 minutes. At the end of this time, g.c. showed that the mixture contained (peak areas) ~10% of 2-chloro-6-fluorophenol, ~3% of a dichlorofluorophenol, a trace of 4-chloro-2-fluorophenol, and a single product peak. This mixture was poured into aqueous base (~1% NaOH) and the resulting mixture extracted with ether (2×300 ml). The ether extracts were combined, washed with water (an emulsion formed which required a little saturated aqueous NaCl to break), dried (MgSO4) and the solvent removed to give an orange-red oil (34 g). $^{19}F$ NMR (CDCl3) showed that essentially a single isomer to be present. The material was subjected to Kugelrohr distillation (oven temp.=135°–145°) to give the desired product as a light yellow oil (32 g): RI=1.6038 @ 25° C. Recrystallization from hexane (freezer) gave the product as a white solid: m.p.=55°–57°C.

The carbon, hydrogen and nitrogen content was:

|  | Carbon | Hydrogen | Nitrogen |
|---|---|---|---|
| Calculated: | 53.85 | 2.64 | 5.23 |
| Found: | 53.70 | 2.54 | 5.16 |

Step 2C

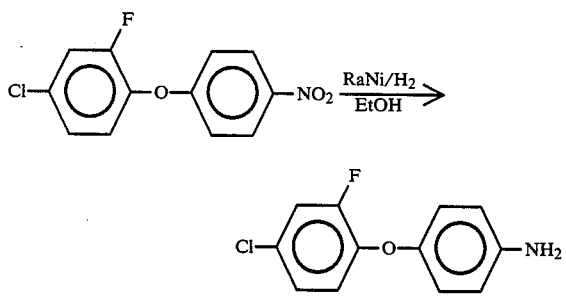

Raney Nickel, i.e., RaNi (3 scoopulas) was washed with water (2×300 ml) and then ethanol (2×300 ml). To this was added a solution of the phenoxynitrobenzene (29 g; 0.108 g) in ethanol (250 ml). The resulting mixture was hydrogenated in a Paar apparatus (initial H2 pressure=50 psi) until the theoretical amount of hydrogen had been taken up (3–4 hours). The mixture was filtered and the solvent evaporated from the filtrate to give 25 g of a light yellow oil which solidified upon standing. An analytical sample was prepared by recrystallization from hexane: m.p.=85.5°–87° C.

The carbon, hydrogen and nitrogen content was:

|  | Carbon | Hydrogen | Nitrogen |
|---|---|---|---|
| Calculated: | 60.64 | 3.82 | 5.89 |
| Found: | 60.49 | 3.77 | 5.85 |

Step 2D

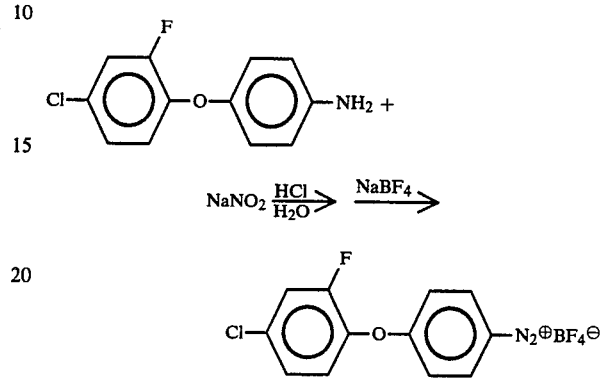

Concentrated hydrochloric acid (35 ml) was added all at once to a mechanically stirred suspension of the aniline (16.64 g; 0.07 mol) in water (70 ml) and the resulting mixture cooled to ≦5° C. in an ice bath. To this stirred mixture was slowly added (dropwise) a solution of sodium nitrite (5.0 g; 0.072 mol) in water (10 ml). The temperature was maintained at ≦8° C. during the addition. By the time the addition was complete, the mixture was essentially homogeneous. After stirring at ≦5° C. for an additional 30 minutes, the solution was treated with charcoal, then filtered through celite. The filtrate was again stirred mechanically at ≦5° C. (ice bath) and a solution of sodium fluoroborate (10.98 g; 0.1 mol) in water (35 ml) was added rapidly. A solid separated immediately. After stirring for an additional 15 minutes, the solid was filtered, washed with a small amount of ice water, then with cold ether (3×150 ml). The solid was air dried for an hour, then completely dried in a vacuum oven over P2O5 at 80° C. for 3 hours. There was thus obtained the desired diazonium tetrafluoroborate (19 g; 84.7%) as an off-white solid. The NMR (d6 acetone or CF3CO2H) of this material was consistent with the assigned structure and showed a low field, two-proton doublet for the protons ortho to the diazonium salt. This material was used directly in subsequent reactions. (Step 2E of Example 2 and Example 3).

Step 2E

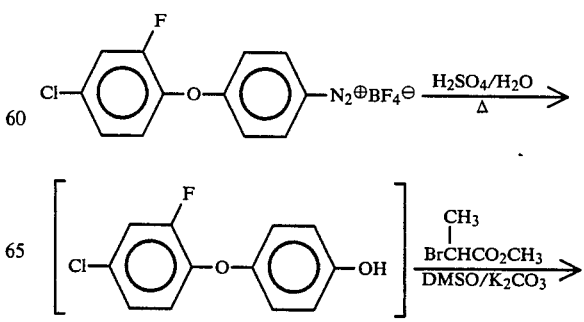

-continued
Step 2E

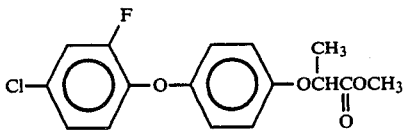

To a stirred solution of concentrated sulfuric acid (8 ml) in water (32 ml) which was heated to a gentle boil, was slowly added the above tetrafluoroborate diazonium salt (from Step 2D) (4 g; 0.0125 mol). After the addition was complete, stirring and heating was contained for 45 minutes, then the reaction poured into ice-water (~300 ml). The mixture was then extracted with ether (3×100 ml), the combined extracts dried (MgSO$_4$) and the solvent evaporated to give 1.2 g of a red oil. Thin layer chromotography (TLC) (silica gel, 7:3 hexane-ethyl acetate) and g.c. showed that this was one main product (phenol) contaminated by a minor product. This red oil was dissolved in DMSO (10 ml), and then methyl 2-bromopropionate (0.9 g, 0.0054 mol) and potassium carbonate (0.84 g; 0.006 mol) was added and the resulting mixture stirred under an inert atmosphere overnight. After the addition of water (200 ml), the mixture was extracted with ether (2×75 ml). The combined ether extracts were washed with water (75 ml), dried (MgSO$_4$) and the solvent removed to give 1.3 g of a red oil. NMR (CDCl$_3$) of this material was consistent with the desired 2-[4-(4-chloro-2-fluorophenoxy)-phenoxy]propionic acid methyl ester. The oil was chromatographed (130 g silica gel, 7:3 hexane-acetone), but this failed to remove the color. The material was taken up in methanol, treated with charcoal, filtered and evaporated to give a yellow oil: RI=1.5509.

EXAMPLE 3

Preparation of 4-(4-chloro-2-fluorophenoxy)phenol

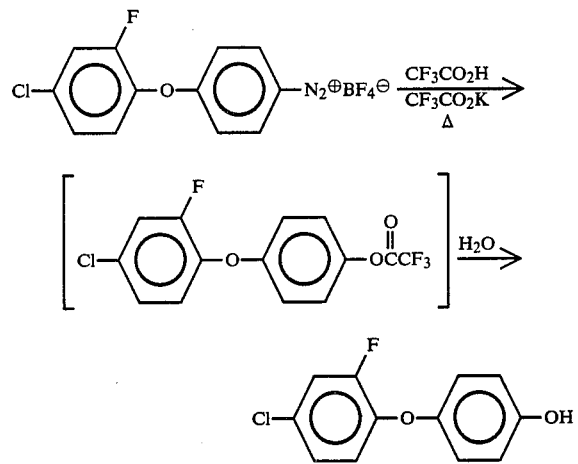

A solution of potassium trifluoroacetate (0.03 mol) in trifluoroacetic acid (TFA) (60 ml) was prepared by the careful addition of potassium carbonate (2.07 g; 0.015 mol) to the trifluoroacetic acid. To this solution was added, with stirring, the diazonium tetrafluorobate salt prepared in Example 2, Step 2E, (7.5 g; 0.023 mol) and the resulting mixture stirred and heated at reflux for 48 hours. NMR (CF$_3$CO$_2$H) of the reaction mixture indicated that some diazonium salt remained. An additional amount of potassium carbonate (2.07 g; 0.015 mol) was added and heating continued for 24 hours. Again, NMR indicated that a small amount of starting material remained. Additional K$_2$CO$_3$ (2.07 g) was added and heating continued for 24 hours. NMR now showed that the mixture was essentially devoid of starting material. About 30 ml of TFA was removed by distillation and the resulting mixture poured into water (200 ml). This aqueous mixture was stirred at 40°-45° C. for 3 hours to hydrolyze the trifluoroacetate. After cooling, the mixture was extracted with ether (3×100 ml), and the ether extracts were treated with charcoal and then filtered through a short pad of silica gel. The filtrate was evaporated to give a dark viscous residue. This was purified via HPLC (8:2 hexane-ethyl acetate) the second peak being collected. Removal of the solvent gave a viscous red oil which was homogeneous by TLC and g.c. NMR (CDCl$_3$) was consistent with the assigned structure. This material solidified upon standing for several days. The methodology employed in this example is analogous to the methods described in D. E. Horning et al., Can. J. Chem., 51, 2347 (1973).

EXAMPLE 4:

Preparation of the R enantiomer of 2-[4-(4-chloro-2-fluorophenoxy)phenoxy]propionic acid methyl ester

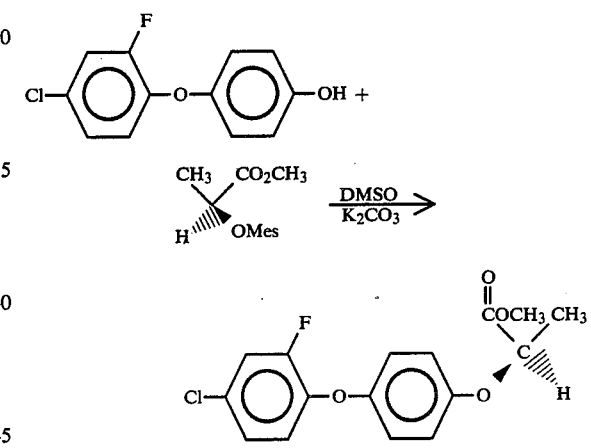

A mixture of 4-(4-chloro-2-fluorophenoxy)-phenol (2.23 g; 0.01 mol), the methanesulfonate of S-methyl lactate (18.22 g; 0.1 mol, minimum of 90% optical purity), and potassium carbonate (1.4 g; 0.01 mol) in DMSO (75 ml) was stirred at room temperature for 18 hours. After this period, the mixture was poured into water (500 ml) then extracted into ether (3×100 ml). The ether extracts were dried (MgSO$_4$), and the solvent evaporated. The residue was purified by preparative HPLC using 8:2 hexane-ethylacetate as the eluent. The first peak to elute (after the solvent front) was collected and the solvent evaporated. This gave 2.3 g (71%) of a light yellow oil whose $^1$H and $^{19}$F NMR (CDCl$_3$) were consistent with the assigned structure. This material possessed an optical rotation of +24.68° as measured at 25° C. The refractive index was 1.5466. Attempts to measure the optical purity using the optically active NMR shift reagent tris-[3-(trifluoromethylhydroxymethylene)-d-camphorateo]europium (III) were not successful. Based upon the optical purity of the starting lactate the optical purity is estimated to be between 75 and 95%.

EXAMPLE 5

Preparation of 2-[4-(4-bromo-2-fluorophenoxy)phenoxy]propionic acid methyl ester Step I

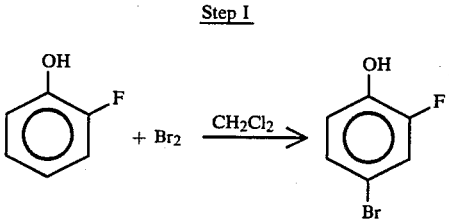

To a stirred solution of 2-fluorophenol (22.4 g, 0.2 mol) in methylene chloride (250 ml) which was cooled to ~3° C. in an ice bath, was added, all at once, bromine (31.97 g, 0.2 mol). The resulting solution was stirred at ice bath temperature for two hours and then at room temperature for 1 hour. The mixture was poured into water (600 ml) containing excess sodium bisulfite. The organic phase was separated and the aqueous phase was washed with additional methylene chloride (200 ml). The combined organic extracts were washed with saturated sodium bicarbonate, dried (MgSO4) and the solvent evaporated to give the desired 2-fluoro-4-bromophenol as a colorless oil (34.5 g, 90%). The NMR (CDCl3) was consistent with the assigned structure. The gc of this material showed that it contained only a trace of the 2,6-isomer. This material was used directly in the following step without additional purification.

Step II

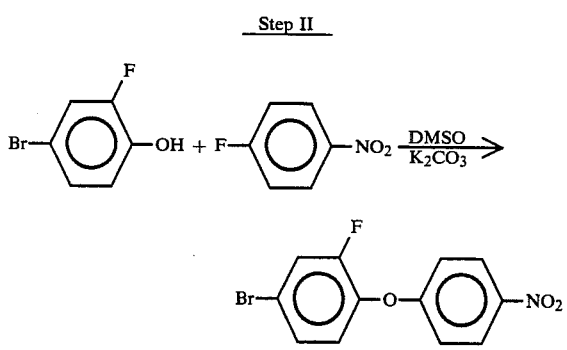

To a stirred mixture of 2-fluoro-4-bromophenol (34.0 g, 0.178 mol), and 4-fluoronitrobenzene (25.12 g, 0.178 mol) in DMSO (250 ml) was added powered potassium carbonate (27.8 g, 0.2 mol). The resulting mixture was maintained under an atmosphere of argon and warmed to 100° C. (oil bath temp) for one hour. After cooling, the mixture was poured into an ice-cold, 1N NaOH solution (1000 ml) and extracted with ether (3×250 ml). The ether extracts were combined, washed with water (300 ml), dried (MgSO4) and the solvent evaporated to give a yellow oil. This material was crystallized from hexane-ether to yield 44.5 g (80%) of the desired product as a light yellow crystalline solid: m.p.=62°-64° C.; NMR (CDCl3) was consistent with the assigned structure. The carbon, hydrogen and nitrogen content was as follows:

|  | Carbon | Hydrogen | Nitrogen |
| --- | --- | --- | --- |
| Calculated: | 46.18 | 2.26 | 4.49 |
| Found: | 46.11 | 2.22 | 4.50 |

Step III

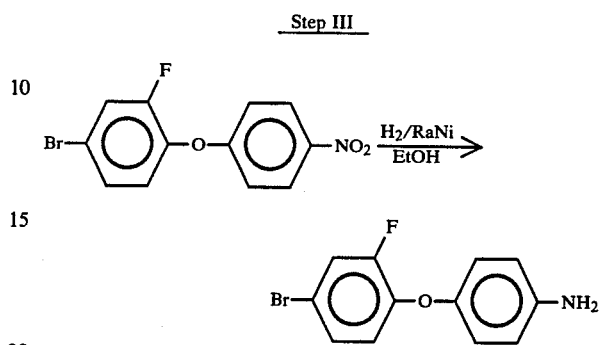

Raney nickel (3 spoonulas) was washed with water (3×250 ml) and then ethanol (3×200 ml). To the catalyst covered with a small amount of ethanol, was added a solution of the 4-(4-bromo-2-fluorophenoxy)nitro benzene from Step III (9.36 g, 0.03 mol) dissolved in warm ethanol (75 ml). The solution was degassed with argon, then hydrogenated on a Parr apparatus with an initial hydrogen pressure of 50 psi. When the theoretical volume of hydrogen had been consumed (~90 minutes), the mixture was degassed, and the catalyst removed via filtration (celite). The solvent was evaporated to give a white solid. Upon recrystallization of this material from methylcyclohexane, it took on an orange coloration and the recrystallized product was tinted orange. A small amount which was recrystallized from hexane did not undergo this apparent slight decomposition. Regardless of the color, the NMR (CDCl3) was consistent with the desired product: m.p.=98°-99.5° C.; Yield=7.7 g(91%). The carbon, hydrogen and nitrogen content was as follows:

|  | Carbon | Hydrogen | Nitrogen |
| --- | --- | --- | --- |
| Calculated: | 51.08 | 3.22 | 4.97 |
| Found: | 51.10 | 3.09 | 4.80 |

This material was used in the next reaction step.

STEP IV

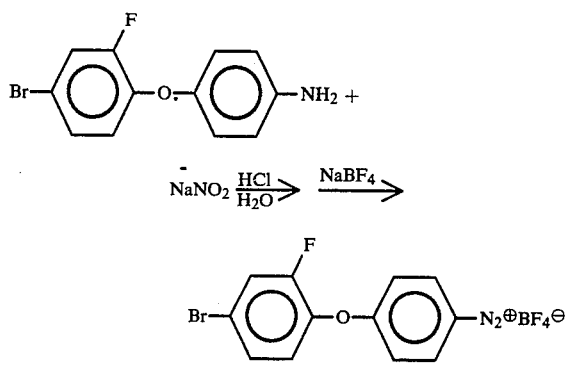

Concentrated hydrochloric acid (50 ml), (was added all at once to a stirred suspension of 4-(4-bromo-2-fluorophenoxy)aniline (30 g, 0.106 mol) in water (110 ml). The resulting mixture was cooled to ~3° C. in an ice bath and then a solution of sodium nitrite (8.07 g, 0.117 mol) in water (15 ml) was slowly added. During the addition, the temperature was maintained at ≦8°C. When all of the sodium nitrite had been added, the mixture had become a homogeneous solution. After the addition was complete, the mixture was stirred at 3° C. for 20 minutes, treated with charcoal, and filtered through celite. The cold filtrate was poured into a 1-liter erlynmeyer flask (wide-mouth), equipped with a mechanical stirrer, and cooled in an ice bath. To this solution, vigorously stirred, was added a solution of sodium fluoroborate (17.6 g, 0.16 mol) in water (50 ml). A white precipitate separated immediately and the mixture was almost too thick to stir. Stirring was continued for 15 minutes, then the product filtered (medium porosity funnel), washed with several portions of ice water and then with cold ether (3×100 ml). After air drying for 30 minutes, the product was dried in a vacuum oven over $P_2O_5$ at 80° C. for 3 hours. There was thus obtained 37.5 g (84%) of the desired diazonium salt, i.e., 4-(4-bromo-2-fluorophenoxy)phenyl diazonium tetrafluoroborate as a white solid. The NMR ($CF_3CO_2H$) was consistent with the assigned structure. This material was used directly in the next reaction step.

STEP V

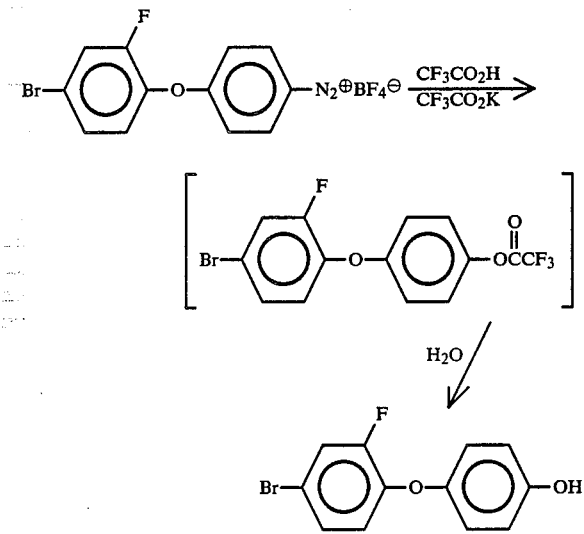

Potassium carbonate (34.78 g, 0.25 mol) was carefully and slowly added to trifluoroacetic acid (200 ml). After the reaction had ceased, the diazonium salt (37 g, 0.097 mol) from Step IV was added, and the stirred solution heated at reflux for 18 hours. At the end of this period, the NMR of the reaction mixture showed the absence of any starting diazonium salt. About half of the trifluoroacetic acid was distilled, then the residue poured into water (600 ml). This mixture was stirred at 50°–60° C. for 1 hour, cooled, and extracted with ether (3×200 ml). The ether extracts were combined, washed with water, and then with saturated sodium bicarbonate (3×300 ml). The sodium bicarbonate wash was conducted carefully because of the generation of foam. The ether phase was then treated with charcoal and filtered through a short pad of silica gel. The ether was removed to give a yellow-orange oil. The pure phenol was obtained by prep HPLC (7:3 hexane-ethylacetate) with the second peak being collected (1-recycle). Removal of the solvent gave the desired product as an orange oil (19 g, 69%) whose NMR was consistent with the assigned structure. RI=1.6056 @ 25° C. The carbon and hydrogen content was as follows:

|  | Carbon | Hydrogen |
|---|---|---|
| Calculated: | 50.91 | 2.85 |
| Found: | 51.20 | 2.89 |

STEP VI

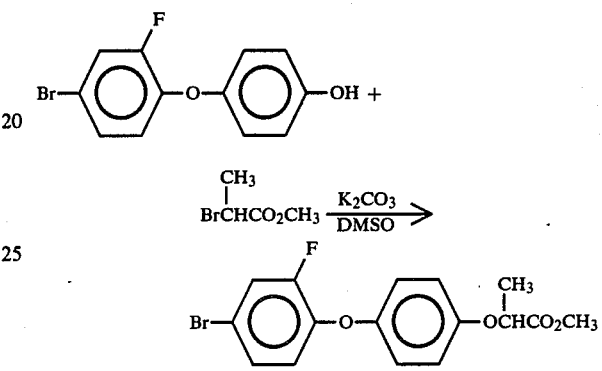

A mixture of the 4-(4-bromo-2-fluorophenoxy)phenol (5.66 g, 0.02 mol) from Step V, methyl 2-bromoproprionate (3.34 g, 0.02 mol) and potassium carbonate (3.06 g, 0.22 mol) in DMSO (30 ml) was stirred, under an atmosphere of nitrogen, at room temperature for 18 hours. The mixture was poured into water (300 ml), and the resulting mixture extracted with ether (2×100 ml). The ether extracts were combined, washed with water (100 ml), dried ($MgSO_4$), and the solvent evaporated to give the desired 2-[4-(4-bromo-2-fluorophenoxy)-phenoxy]propionic acid; methyl ester as a yellow oil (6.0 g, 81%); RI=1.5628; NMR ($CDCl_3$) was consistent with the assigned structure. The carbon and hydrogen content was as follows:

|  | Carbon | Hydrogen |
|---|---|---|
| Calculated: | 52.05 | 3.82 |
| Found: | 52.12 | 3.64 |

EXAMPLE 6

Preparation of the R enantiomer of 2-[4-(4-bromo-2-fluorophenoxy)phenoxy]-propionic acid methyl ester

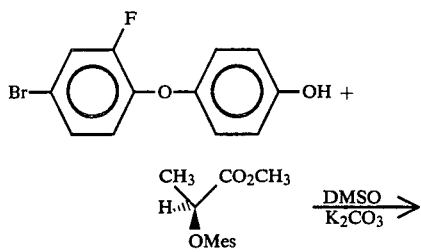

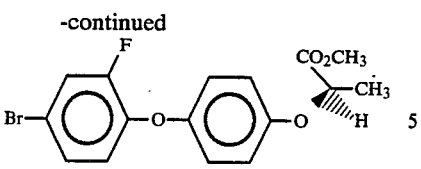

A mixture of the 4-(4-bromo-2-fluorophenoxy)-phenol (2.83 g, 0.01 mol), the methanesulfonate of S methyl lactate (18.2 g, 0.01 mol), and potassium carbonate (1.67 g, 0.012 mol) in DMSO (70 ml) was stirred at room temperature for 40 hours, then poured into water (700 ml). The mixture was extracted with ether (2×200 ml). Pentane (100 ml) was added to the combined ether extracts and the resulting solution washed with water (300 ml). The organic phase was dried (MgSO$_4$) and the solvent evaporated to give a light yellow oil (~7 g). This oil was purified via prep HPLC (8:2 hexane-acetone) with the first peak being collected. Removal of the solvent gave the desired product enriched in the "R" enantiomer; Optical rotation=+20.34° @ 25° C. RI=1.5614 @ 25° C.; NMR (CDCl$_3$) was identical with that obtained in Example 4. No attempt was made to determine the optical purity of this material.

EXAMPLE 7

Preparation of 2-(4-(4-Bromo-2-fluorophenoxy)-phenoxy)propionic acid

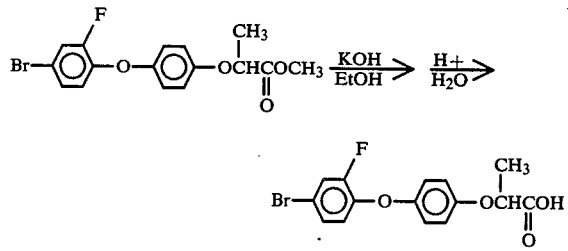

A solution of the methyl ester from Example 5 (76 g, 0.206 mol) in ethanol (200 ml) was added to a stirred solution of potassium hydroxide (26.4 g, 85% KOH, 0.4 mol) in ethanol (250 ml). The resulting mixture was stirred for 30 minutes, then the solvent evaporated. The residue was dissolved in water (200 ml), the resulting solution acidified with concentrated hydrochloric acid, and then extracted with ether. The ether extracts were dried (MgSO$_4$) and then the solvent evaporated to give the crude acid as an off-white solid. Recrystallization from methylcyclohexane gave 68 g (93%) of the desired acid as a light tan solid. An analytical, sample was prepared by a second recrystallization from methylcyclohexane: m.p.=120°–121° C. Calc. C: 50.72; H: 3.41. Found: C: 50.84; H: 3.46.

EXAMPLE 8

Preparation of 2-(4-(4-Bromo-2-fluorophenoxy)-phenoxy)propionyl chloride

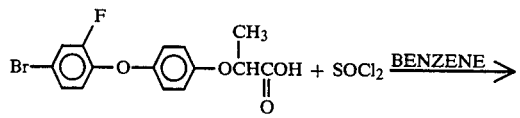

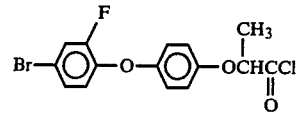

A stirred mixture of the acid from Example 7 (61.8 g, 0.174 mol), benzene (500 ml), thionylchloride (21.77 g, 0.183 mol) and dimethylformamide (DMF, 2 ml) was heated at reflux for one hour. After cooling, all volatile material was evaporated to give a quantitative yield of the crude acid chloride as a bronze colored oil. This material was used in subsequent reactions without further purification.

EXAMPLE 9

Preparation of Propionic acid: 2-(4-(4-bromo-2-fluorophenoxy)phenoxy), n-butyl ester

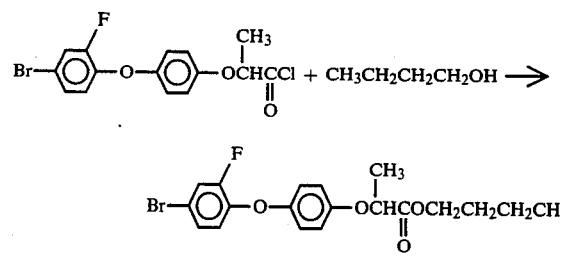

To a stirred solution of n-butyl alcohol (0.75 g, 0.01 mol), pyridine (0.8 g, 0.01 mol), and 4-dimethylaminopyridine (DMAP, catalytic amount) in dry ether (30 ml) was slowly dropped a solution of the acid chloride (3.73 g, 0.01 mol) in ether (10 ml). After the addition was complete, the stirred mixture was heated at reflux for one hour, cooled, then poured into cold 2N HCl (100 ml). The ether phase was separated, washed with saturated sodium bicarbonate solution, treated with charcoal, then filtered through a pad of silica gel. The filtrate was dried (MgSO$_4$) and the solvent evaporated to give the ester as a light yellow oil (3.7 g, 90%): Refractive Index (RI)=1.5409 @ 25° C. Calc. C: 55.48; H: 4.90. Found C: 55.74; H: 4.94.

In a similar manner the following esters were prepared:

CHART I

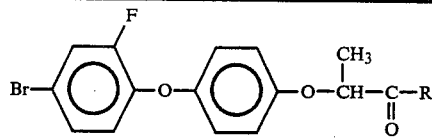

| R | RI or MP | Analysis Calc'd | Found |
|---|---|---|---|
| —OCH$_2$CH$_2$OCH$_2$CH$_3$ | 1.5411 | C, 53.41 | 53.50 |
|  |  | H, 4.72 | 4.74 |
| —OCH$_2$(CH$_2$)$_6$CH$_3$ | 1.5275 | C, 59.10 | 59.26 |
|  |  | H, 6.04 | 5.93 |
| —OCH$_2$CH$_2$N(CH$_3$)$_2$ | 1.5461 | C, 53.53 | 53.59 |
|  |  | H, 4.97 | 5.01 |
|  |  | N, 3.29 | 3.30 |
| 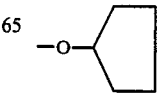 | 1.5531 | C, 56.75 | 56.89 |
|  |  | H, 4.76 | 4.91 |

CHART I-continued

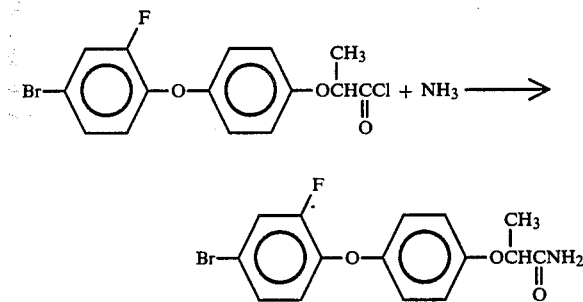

| R | RI or MP | Analysis Calc'd | Found |
|---|---|---|---|
| —OCH$_2$CH=CH$_2$ | 1.5555 | C, 54.70 | 54.94 |
| | | H, 4.08 | 4.12 |
| —OCH$_2$C≡CH | 1.5633 | C, 50.40 | 53.58 |
| | | H, 3.95 | 3.62 |
| —O-C$_6$H$_4$-CH$_3$ (o-tolyloxy) | 1.5780 | C, 59.34 | 58.83 |
| | | H, 4.07 | 3.83 |
| —S-C$_6$H$_5$ | 1.6031 | C, 56.38 | 57.20 |
| | | H, 3.61 | 3.63 |

EXAMPLE 10

Preparation of 2-(4-(4-Bromo-2-fluorophenoxy)phenoxy)propionamide

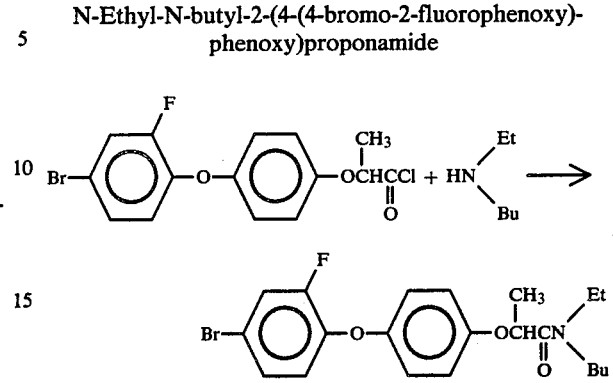

To a cold (approx. 5° C.), stirred mixture of concentrated aqueous ammonia (25 ml) and ethyl acetate (25 ml) was slowly dropped a solution of the acid chloride (3.73 g, 0.01 mol) in ethyl acetate (20 ml). After the addition was complete, the mixture was stirred at room temperature for one hour. The organic phase was separated and the aqueous phase was extracted with a second (50 ml) portion of ethyl acetate. The organic phases were combined, washed with water (75 ml), then with saturated sodium chloride solution (75 ml), and dried (MgSO$_4$). Removal of the solvent gave a quantitive yield of the crude amide as a white solid. Recrystallization from methylcyclohexane gave an analytical sample: m.p.=110°–112° C. Calc: C, 50.87; H, 3.70. Found: C, 51.00; H, 3.75.

EXAMPLE 11

Preparation of N-Ethyl-N-butyl-2-(4-(4-bromo-2-fluorophenoxy)phenoxy)proponamide To a stirred solution of N-ethyl-N-butylamide (2.12 g, 0.021 mol) and 4-dimethylaminopyridine (catalytic amount) in ether (30 ml) was slowly dropped a solution of the acid chloride (3.73 g, 0.01 mol) in ether (10 ml). After the addition was complete, the mixture was stirred and heated at reflux for 30 minutes cooled, then poured into 2N hydrochloric acid (100 ml). The ether phase was separated and the aqueous phase washed with additional ether (50 ml). The organic phases were combined, washed with saturated sodium bicarbonate (100 ml), treated with charcoal, then filtered through a short pad of silica gel. The filtrate was dried (MgSO$_4$) and the solvent evaporated to give 3.9 g (89%) of the desired amide as a light yellow oil: RI=1.5512 @ 25° C. Calc: C, 57.54; H, 5.75. Found: C, 57.55; H, 5.77.

The following derivatives were prepared in a similar manner.

CHART II

| R | RI or MP | Analysis Calc'd | Found |
|---|---|---|---|
| —N(CH$_3$)(Ph) | 1.5944 | C, 59.47 | 59.09 |
| | | H, 4.31 | 4.19 |
| | | N, 3.15 | 2.93 |
| —NCH$_2$CH=CH$_2$ | 1.5730 | C, 54.83 | 54.66 |
| | | H, 4.35 | 4.21 |
| | | N, 3.55 | 3.44 |
| —NHCH(CH$_3$)$_2$ | 101–104° C. | C, 54.56 | 55.28 |
| | | H, 4.83 | 4.78 |
| | | N, 3.54 | 3.52 |
| —NH-C$_6$H$_4$-CF$_3$ | 137–139° C. | C, 53.03 | 53.14 |
| | | H, 3.24 | 3.16 |
| | | N, 2.81 | 2.76 |
| —NH-C$_6$H$_3$(CH$_3$)(Cl) | 69.5–71° C. | C, 55.19 | 55.33 |
| | | H, 3.79 | 3.51 |
| | | N, 2.93 | 2.93 |

CHART II-continued

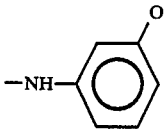

| R | RI or MP | Analysis Calc'd | Found |
|---|---|---|---|
| 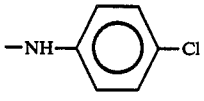 | 54–55° C. | C, 57.40<br>H, 4.16<br>N, 3.04 | 58.04<br>4.34<br>3.12 |
| 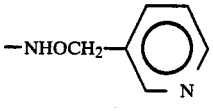 | 127–129° | C, 54.27<br>H, 3.47<br>N, 3.07 | 54.12<br>3.38<br>2.87 |
| 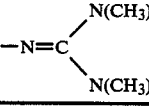 | 1.5954 | C, 54.68<br>H, 3.93<br>N, 6.07 | 54.39<br>3.95<br>6.08 |
| 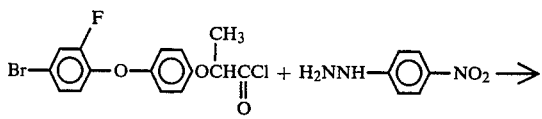 | 1.5840 | C, 53.10<br>H, 5.12<br>N, 9.29 | 52.02<br>5.11<br>9.05 |

EXAMPLE 12

Preparation of Propionic Acid:
2-(4-(4-bromo-2-fluorophenoxy)phenoxy),
4-nitrophenylhydrazide

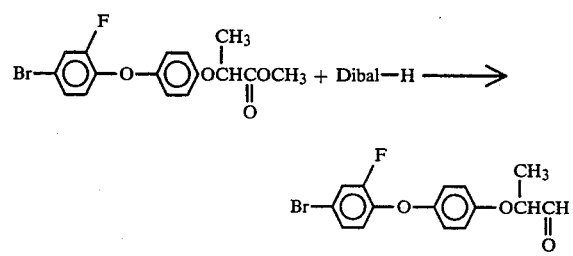

To a stirred solution of 4-nitrophenylhydrazine (3.06 g, 0.02 mol) and 4-dimethylaminopyridine (catalytic amount) in tetrahydrofuran (THF, 40 ml) was slowly dropped a solution of the acid chloride (3.73 g, 01 mol) in THF (10 ml). After the addition was complete, the mixture was stirred for 30 min at room temperature, then poured into 0.5N hydrochloric acid (150 ml). The product was extracted into ether. The ether phase was treated with charcoal, filtered through a short pad of silica gel, dried (MgSO₄), then the solvent evaporated to give the desired hydrazide (4.2 g, 89%) as an orange solid. Recrystallization from a small volume of toluene gave an analytical sample: m.p.=177°–180° C. Calc: C, 51.45; H, 3.50; N, 8.57. Found: C, 51.63; H, 3.30; N, 8.69.

EXAMPLE 13

Preparation of Methyl
2-(4-(2,4-difluorophenoxy)phenoxy)propionate

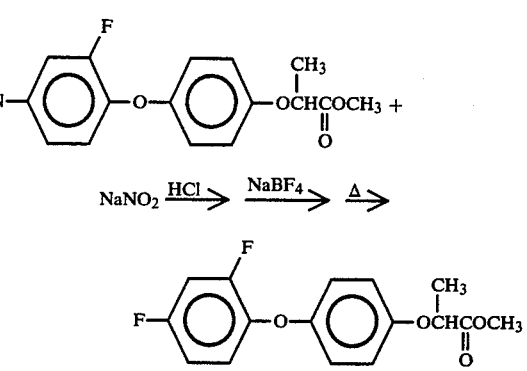

To a cold (less than 5° C.) stirred solution of the aniline (6.11 g, 0.02 mol), concentrated hydrochloric acid (6 ml), and water (50 ml) was slowly dropped a solution of sodium nitrite (1.52 g, 0.022 mol) in water (10 ml). After the addition was complete, the mixture was stirred for 15 minutes then quickly filtered through celite to remove some insoluble material. The insoluble material was washed with several portions of ice water. To the cold (less than 5° C.), vigorously stirred filtrate and washings, was added a solution of sodium tetrafluoroborate (4.39 g, 0.04 mol) in water (50 ml). The yellow solid which separated was filtered, washed with ether, then dried overnight on a porous plate. The dried, solid diazonium tetrafluoroborate (7.5 g) was placed in a 250 ml round bottom flask and heated at 190°–200° C. for approximately 5 min. As the salt melted it decomposed with gas evolution. After cooling, the dark residue was taken up in ether (150 ml), washed with saturated sodium bicarbonate, dried (MgSO₄) and purified by preparative HPLC using 8:2 hexane/ethyl acetate as the eluent. This first component to elute was collected, and the solvent evaporated to give the desired difluorophenoxyphenoxypropionate as a light yellow oil (1.6 g, 28%); RI=1.5276 @ 25° C. Calc: C, 62.33; H, 4.58. Found: C, 62.31; H, 4.43.

EXAMPLE 14

Preparation of
2-(4-(4-Bromo-2-fluorophenoxy)phenoxy)propionaldehyde

Br—⌬—F—O—⌬—OCHCOCH₃ + Dibal—H ⟶
        |
        CH₃
        ‖
        O

Br—⌬—F—O—⌬—OCHCH
        |      ‖
        CH₃   O

A stirred solution of the ester (3.7 g, 0.01 mol) in toluene (150 mol), under an atmosphere of nitrogen, was cooled to −78° C. using a dry ice/acetone cooling bath. To this was slowly dropped a solution of diisobutylaluminum hydride (Dibal-H, 11 ml of 1.2M solution, 0.013 mol) in toluene. During the addition the temperature was maintained at less than −70° C. After the addition was complete, the mixture was stirred an additional hour. While maintaining the temperature at less than −70° C. the reaction was quenched by the slow addition of a 75:25:6 ether/acetic acid/water solution (11 ml). The mixture was then warmed to room temperature, filtered (filter aid necessary), and the solvent evaporated. The oily residue was taken up in ether and passed through a short column of silica gel. Removal of the solvent gave the desired aldehyde (3.0 g) as a clear oil: RI=1.5794 @ 25° C. Calc: C, 53.11; H, 3.57. Found: C, 52.99; H, 3.62.

The oxime, —CH=NOH, was prepared from the above aldehyde by standard procedures. It is a glass, having a RI=1.5811. Calc: C, 50.87; H, 3.70; N, 3.96. Found: C, 51.21; H, 3.73; N, 3.89.

Similarly, the ethylene glycol acetal,

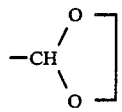

was prepared from the above aldehyde by standard procedures. It is a light yellow oil having a RI=1.5678. Calc: C, 53.28; H, 4.21. Found: C, 53.61; H, 4.08.

EXAMPLE 15

Preparation of 2-(4-(4-Bromo-2-fluorophenoxy)-phenoxy)propanol

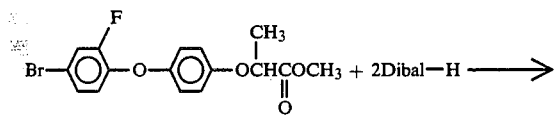

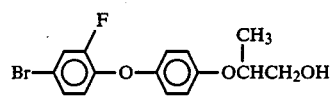

In a manner similar to the reduction described above, the ester was reduced to the corresponding alcohol using slightly more than two equivalents of Dibal-H. There was thus obtained the desired propanol as a light yellow oil: RI=1.5780 @ 25° C. Calc: C, 52.80; H, 4.14. Found: C, 53.0; H, 4.04.

The benzoate ester,

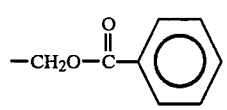

was prepared from the above alcohol by standard procedures. It is a light yellow oil, RI=1.5798. Calc: C, 59.34; H, 4.07. Found: C, 59.35; H, 4.02.

EXAMPLE 16

Preparation of N-Methanesulfonyl-2-(4-bromo-2-fluorophenoxy)-phenoxy)propionamide

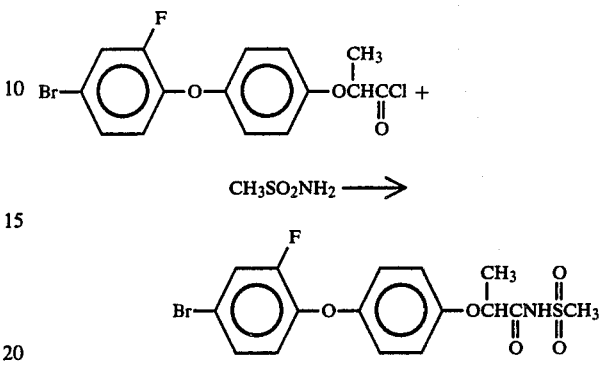

To a stirred solution of methanesulfonamide (1.5 g, 0.016 mol), and 4-dimethylaminopyridine (catalytic amount) in pyridine (20 ml) was slowly added, in a dropwise manner, the neat acid chloride (3.7 g, 0.01 mol). The reaction mixture was stirred for 5 days at room temperature, then poured into cold, 2N hydrochloric acid (250 ml). The resulting mxiture was extracted with ether (2×100 ml) and the aqueous phase discarded. The ether phase was then extracted with saturated sodium bicarbonate (2×50 ml) and the ether phase discarded. The aqueous phase was acidified to pH less than 4 with concentrated hydrochloric acid. The aqueous mixture was extracted with ether, the ether phases combined, dried (MgSO4) and the solvent evaporated to give the desired product as a white solid: m.p. 101°-103° C. Calc: C, 44.46; H, 3.50; N, 3.24. Found: C, 44.45; H, 3.40; N, 3.16.

EXAMPLE 17

Preparation of Propanimidothioic Acid: 2-(4-(4-bromo-2-fluorophenoxy)phenoxy)-N-(1-methylethyl)-ethyl)-ethyl ester

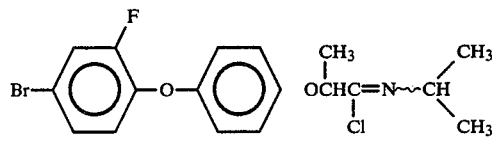

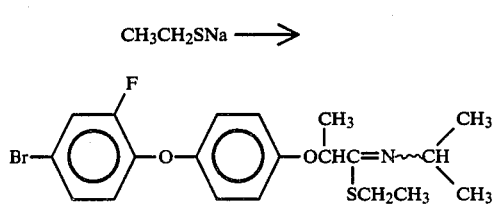

To a solution of the imide chloride (2.7 g, 0.007 mol) (prepared by heating a solution of the compound in Chart II where R is —NHCH(CH3)2 with a 10% excess of phosphorous pentachloride in chloroform for twenty four hours, then evaporating all volatile material) in dry tetrahydrofuran (50 ml) was added solid sodium ethyl mercaptide (1.85 g, 0.022 mol) in one portion. The resulting slurry was stirred overnight at room temperature, then poured into ice water. The organic phase was separated, and the aqueous phase was washed with ether. The organic phases were combined, dried (MgSO₄), and the solvent evaporated. The residue was purified via preparative HPLC (9:1 hexane/acetone as solvent). The first peak to elute was collected and the solvent evaporated to give 1.0 g (32%) of a yellow oil: RI=1.5659 @ 25° C. The NMR (CDCl₃) of this material showed that it consisted of a 55:45 mixture of the syn and anti isomers of the desired thioiminoether. Calc: C, 54.55; H, 5.26 N, 3.18. Found: C, 54.84; H, 5.09; N, 3.03.

EXAMPLE 18

Preparation of Morpholine:
4-(2-(4-(4-bromo-2-fluorobenoxyl)phenoxy)-1-((1-methylethyl)-imino)propyl

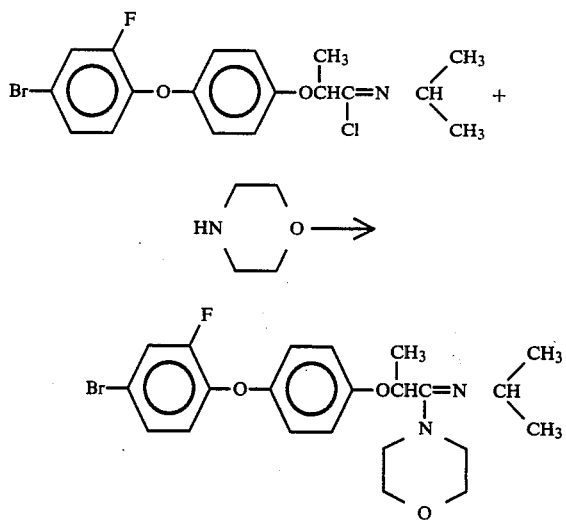

In a manner similar to that described above, the imide chloride was condensed with an excess of morpholine in boiling ether. After filtration, and evaporation of the solvent, the residue was partitioned between ether and 2N hydrochloride acid. The ether phase was discarded, and the product isolated from the aqueous acid by adjusting the pH to 10, and ether extraction. Drying (MgSO₄) and removing the solvent, gave the desired morpholinoamidine as a viscous yellow oil (1.1 g, 35%): RI=1.5610 @ 25° C. The NMR (CDCl₃) of this material showed it to be a mixture of syn and anti isomers. Calc: C, 56.78; H, 5.63; N, 6.02. Found: C, 56.95; H, 5.39; N, 5.89.

EXAMPLE 19

Preparation of
2-(4-(4-Bromo-2-fluorophenoxy)-phenoxy)propanoyl nitrile

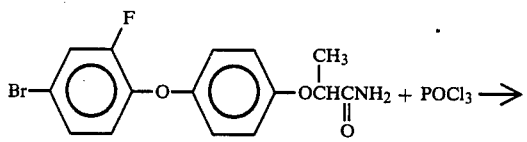

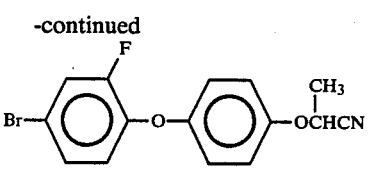

A solution of the amide (1.8 g, 0.0051 mol) and phosphorous oxychloride (POCl₃, 0.86 g, 0.0056 mol) in acetonitrile (20 ml) was stirred and heated at reflux for one hour, then additional POCl₃ (0.5 g) added. After heating for an additional hour, the cooled reaction mixture was poured into ice water (300 ml). The aqueous mixture was stirred for a few minutes, then extracted with ether. The ether extracts were washed with saturated sodium bicarbonate, treated with charcoal, dried (MgSO₄) and the solvent evaporated to give 1.4 g (82%) of the desired nitrile as a light yellow oil: RI=1.5691 @ 25° C. Calc: C, 53.59; H, 3.30; N, 4.17. Found: C, 53.61; H, 3.31; N, 4.21.

Alternatively, various compounds within the scope of the present invention may be prepared as illustrated by the following examples and by employing appropriate starting materials.

EXAMPLE 20

Preparation of Methyl
2-(4-(2-Fluoro-4-nitrophenoxy)phenoxy)proprionate

A stirred mixture of 3,4-difluoronitrobenzene (13.5 g, 0.85 mol), methyl 2-(4-hydroxyphenoxy)-propionate (23.1 g, 0.085 mol), and potassium carbonate (12.5 g, 0.09 mol) in DMSO (200 ml) was heated in an oil bath (120° bath temperature) for one hour. After cooling the reaction mixture was poured into ice water (1000 ml) and the resulting mixture was extracted with ether (3×200 ml). The ether extracts were combined, pentane (200 ml) added, and the resulting solution washed with 5% sodium hydroxide solution (200 ml), then with water. After drying (MgSO₄), the solvent was evaporated to give 28 g (98%) of the desired product as a light-yellow oil which solidified upon standing. Recrystallization from hexane-ether gave an analytical sample: m.p.=67.5°-69° C.; Calc: C, 57.31; H, 4.21; N, 4.18. Found: C, 57.00; H, 4.13; N, 4.11.

EXAMPLE 21

Preparation of Methyl
2-(4-(4-Amino-2-fluorophenoxy)phenoxy)propionate

A solution of the nitro-compound (21.7 g, 0.065 mol) in ethyl acetate (200 ml) containing 5% palladium on charcoal (1.0 g) was subjected to hydrogenation on a Paar shaker (initial pressure=50 psi) until the theoretical amount of hydrogen had been consumed. The catalyst was removed by filtration, and the solvent evaporated to give a quantitative yield of the desired aniline as a light yellow oil: m.p. (HCl salt)=145°-150° C.; Calc (HCl salt): C, 56.23; H, 5.02; N, 4.10. Found: C, 55.92; H, 4.89; N, 4.04.

EXAMPLE 22

Preparation of Methyl
2-(4-(4-Bromo-2-fluorophenoxy)phenoxy)propionate

To a solution of 48% hydrobromic acid (250 ml) and water (350 ml) was rapidly added the phenoxyaniline (92 g, 0.3 mol). The mixture was warmed until the solid, insoluble hydrobromide salt formed. The stirred mixture was cooled to less than 5° C. in an ice bath, then a solution of sodium nitrite (22.8 g, 0.33 mol) in water (40 ml) was slowly added. The addition was such that the reaction temperature was maintained at less than 6° C. After the addition was complete, the mixture was stirred for an additional 15 minutes, then the yellow diazonnium solution was added, in a rapid dropwise manner, to a warm, stirred solution of cuprous bromide (47.3 g, 0.33 mol) in 48% hydrobromic acid (100 ml). The CuBr/HBr solution was maintained at 65°-75° C. by a warm water bath. After all of the diazonnium had been added, the dark mixture was stirred an additional 15 minutes, cooled at room temperature, and extracted with ether. The ether extracts were combined, washed with saturated sodium bicarbonate solution, dried (MgSO4) and the solvent evaporated. The dark, viscous residue was subjected to bulb-to-bulb distillation to give the desired product (64 g, 58%).

EXAMPLE 23

Preparation of Ethyl 4-(4-(4-Chloro-2-fluorophenoxy)phenoxy)pentanoate

A stirred mixture of 4-(4-chloro-2-fluorophenoxy)-phenol (2.3 g, 0.0103 mol), ethyl 4-bromopentanoate (2.01 g, 0.0103 mol), and potassium carbonate (1.46 g, 0.105 mol) in DMF (20 ml) was heated in an oil bath at 130° C. for one hour. Additional bromide (0.5 g) and carbonate (0.5 g) were added each hour for the next four hours. At the end of this period, gas chromatography indicated that most of the starting phenol had reacted. After cooling, the reaction mixture was poured into 4N HCl solution (200 ml), and the product extracted into a 1:1 mixture of ether-pentane (2×150 ml). The organic extracts were combined, washed with 10% NaOH solution (200 ml), dried (MgSO4), then the solvent evaporated. The resulting orange oil was purified via preparative HPLC (9:1 hexane/ethyl acetate) with the second peak being collected. Removal of the solvent gave the desired ester as a light yellow oil: RI=1.5344 @ 25° C. Calc: C, 62.21; H, 5.50. Found: C, 62.38; H, 5.33.

EXAMPLE 24

Preparation of Methyl 4-(4-(Bromo-2-fluorophenoxy)phenoxy)pent-2-enoate

A stirred mixture of 4-(4-bromo-2-fluorophenoxy)-phenol (1.0 g, 0.0035 mol), E methyl 4-bromopent-2-enoate (0.71 g, 0.0037 mol) and potassium carbonate (0.56 g, 0.004 mol) in acetonitrile (15 ml) was heated at reflux for 90 minutes, then poured into ice water. The resulting mixture was extracted with ether (2×100 ml). The ether extracts were combined, treated with charcoal, filtered through a short pad of silica gel, dried (MgSO4), and the solvent evaporated to give the desired product as a yellow oil (1.2 g): RI=1.5660 @ 25° C. Calc: C, 54.70; H, 4.08. Found: C, 54.77; H, 3.79.

EXAMPLE 25

Preparation of Methyl 4-(4-(Iodo-2-fluorophenoxy)phenoxy)propionate

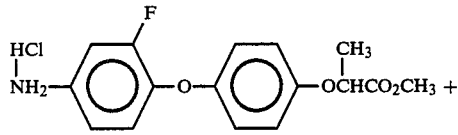

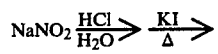

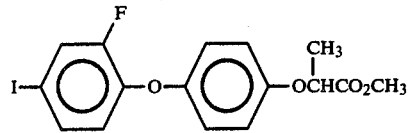

A vigorously stirred mixture of the hydrochloride salt (10.22 g, 0.03 mol) in water (125 mol) and concentrated HCl (7.5 ml) was cooled to ≦5° in an ice bath. This resulted in a thick, almost pasty mixture. To this mixture was slowly added a solution of sodium nitrite (2.22 g, 0.032 mol) in water (6 ml). As the sodium nitrite was added, the reaction mixture became a homogeneous solution (yellow) containing a small amount of insoluble black polymer. After the addition was complete, the reaction mixture was stirred for an additional 10 min., treated with charcoal, and the cold solution quickly filtered through celite. The filtrate was placed in a 500 ml erlenmeyer flask and again cooled in an ice bath. To this stirred solution was carefully added a solution of potassium iodide (5.5 g, 0.033 mol) in water (10 ml)—some foaming resulted. The mixture was stirred at room temperature for 1 hr., then slowly warmed to 60°. The solution containing a dark, viscous gum was cooled to room temperature, then extracted with ether (3 times with 150 ml). The ether extracts were combined, washed with sodium bisulfite solution, dried (MgSO4) and the solvent evaporated. This mixture was purified via HPLC (85:15 hexane:acetone) with the first peak being collected. Removal of the solvent gave a yellow oil (7.7 g, 61.6 percent) whose NMR (CDCl3, $^1$H and $^{19}$F) was consistent with the assigned structure; RI=1.5830 at 25° C. Calc: C, 46.17; H, 3.39. Found: C, 46.88; H, 3.35.

The compounds of the present invention, i.e., active ingredients, have been found to be suitable for use in methods for the preemergent and postemergent control of grasses, such as, barnyard grass, crabgrass, yellow foxtail and johnson grass, in the presence of broadleaf crops, such as, cotton, soybeans and sugar beets. Further, it has been surprisingly found that the compounds of Formula (I) above where X is —Cl or —Br are selective, i.e., exhibit little or no phytotoxic effects, to small grains such as wheat and barley.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomeaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat® 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic® 61 (molecular weight about 1000), polyethylene glycol ester of tall oil acids, sodium octophenoxyethoxyethyl sulfate, tris(polyoxyethylene)sorbitan monostearate (Tween® 60), and sodium dihexylsulfosuccinate.

The concentration of the active ingredients in solid or liquid compositions generally is from 0.003 to 95 percent by weight or more. Concentrations from 0.05 to 50 percent by weight are often employed. In compositions to be employed as concentrates, the active ingredient can be present in a concentration from 5 to 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

Other adjuvants, such as, for example, crop oil and crop oil concentrates, may also be included in the formulated compositions of the invention as is known to those skilled in the art.

The present compositions can be applied by the use of power dusters, boom and hand sprayers, spray dusters, by addition to irrigation water, and by other conventional means. The compositions can also be applied from airplanes as a dust or spray since the active ingredients are effective at very low application rates.

The active ingredients of the present invention have been found to possess desirable herbicidal activity in general against grassy weeds such as foxtail, blackgrass, johnsongrass, wild oats, barnyard grass and crabgrass in preemergent operations and also against the same grasses in postemergent operations. The active ingredients possess desirable herbicidal activity against the grassy weeds, described above, while at the same time are tolerant or selective to broadleaf crops, such as, cotton, soybeans and sugar beets. The compounds of Formula (I) where X is —Cl, and particularly where X is —Br, are surprisingly selective to small grain crops, such as, wheat and barley.

The exact rate to be applied is dependent not only on a specific active ingredient being applied, but also on a particular action desired (e.g., general or selective control), the plant species to be modified, and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from 0.112 to 5.6 kgs/hectare, but higher rates may be appropriate in some cases such as 22.4 kgs/hectare or more. In preemergent operations for selective uses a dosage of 0.112 to 11.2 kgs/hectare or more is generally applicable, a rate of 0.112 to 4.48 kgs/hectare being preferred and 0.112 to 2.24 kgs/hectare being most preferred. For controlling an infestation of annuals, a dosage of 0.112 to 0.56 kgs/hectare is generally utilized. When the infestation consists largely of perennials, a dosage of from 0.112 to 4.48, preferably 0.56 to 2.24 kgs/hectare should be employed.

In postemergent operations a dosage of 0.0112 to 22.4 kgs/hectare or more is generally applicable, although not all compounds are equally effective and some weeds are more difficult to control. A dosage rate in the range of 0.056 to 0.84 kgs/hectare is preferred in selective postemergent control of annual grassy weeds, while about 0.112 to 5.6 kgs/hectare is preferred and more preferably 0.112 to 2.24 kgs/hectare for the selective postemergent control of perennial grassy weeds.

EXAMPLE A

Postemergent Activity

Representative compositions of the present invention were evaluated for the postemergence control of species of plants listed in Table A. In these evaluations, pots of the plant species listed in Table A, grown to a height of about 10 cms, were used. Aqueous spray compositions, containing various amounts of 2-[4-(2-fluoro-4-trifluoromethylphenoxy)-phenoxy]propionic acid methyl ester, i.e., 25 ppm, 62.5 ppm, 31.25 ppm, 15.6 ppm, 7.8 ppm and 3.9 ppm, respectively, were applied to separate pots. The spray compositions were made by mixing the active ingredient in acetone to ½ the final volume, i.e., twice the final concentration. An equal amount of water was added to the active ingredient/acetone mixture wherein the water contained 0.1 percent by weight of TWEEN ® 20 surfactant. The application to the plants was made to the point of run-off and was carried out with conventional spraying equipment. Other pots were sprayed with similar compositions containing no toxicant to serve as controls. Thereafter, the pots were maintained under conditions conducive for plant growth. Two weeks after treatment, the pots were examined for plant growth and evaluated on a scale of 0 to 100 where 0 represents no effect and 100 represents complete kill. The results of the examination of the treated pots are set forth below in Table A.

TABLE A

| Plant | % Control at Indicated Dosage (ppm) | | | | | | |
|---|---|---|---|---|---|---|---|
| | 125 | 62.5 | 31.25 | 15.6 | 7.8 | 3.9 | 0.0 |
| Wheat | 100 | 100 | 100 | 90 | 60 | 0 | 0 |
| Barnyard Grass | 100 | 100 | 100 | 100 | 100 | 50 | 0 |
| Crabgrass | 100 | 100 | 100 | 100 | 100 | 90 | 0 |
| Yellow Foxtail | 100 | 100 | 100 | 100 | 100 | 35 | 0 |
| Johnson Grass | 100 | 100 | 100 | 100 | 100 | 60 | 0 |
| Wild Oats | 100 | 100 | 100 | 60 | 0 | 0 | 0 |

At 125 ppm 2-[4-(2-fluoro-4-trifluoromethylphenoxy)-phenoxy]propionic acid methyl ester was inactive, i.e., no phytotoxic effect, against cotton, rape, soybeans, sugar beets, jimson weed, morning glory, pigweed, velvet leaf and cocklebur.

Results of similar postemergent testing of 2-(4-(2-fluoro-4-iodophenoxy)phenoxy)propionic acid methyl ester were as follows:

| Plant Species | % Control of Indicated Dosage (ppm) | | | |
|---|---|---|---|---|
| | 125 | 62.5 | 31.25 | 15.6 |
| Wheat | 0 | 0 | 0 | 0 |
| Barnyard Grass | 100 | 100 | 85 | 10 |
| Crabgrass | 100 | 100 | 100 | 100 |
| Yellow Foxtail | 100 | 100 | 100 | 90 |
| Johnson Grass | 100 | 100 | 100 | 90 |
| Wild Oats | 0 | 0 | 0 | 0 |

EXAMPLE B

Postemergent Activity

Substantially the same procedures as those described in Example A were repeated except that the active ingredients were 2-[4-(4-chloro-2-fluorophenoxy)-phenoxy]propionic acid; methyl ester and its R-enantiomer and 2-(4-(4-bromo-2-fluorophenoxy)phenoxy propionic acid; methyl ester and its R enantiomer. The results are listed below in Table B.

TABLE B

| Species | % Control at Indicated Dosage (ppm) | | | | | | | | | | | | | |
|---|---|---|---|---|---|---|---|---|---|---|---|---|---|---|
| | 4-Chloro- | | | | | | 4-Bromo- | | | | | | | |
| | 500 | 250 | 125 | 62.5 | 31.25 | 15.6 | 500 | 250 | 125 | 62.5 | 31.25 | 15.6 | 7.8 | 3.9 |
| Wheat | 40 | 0 | 0 | 0 | 0 | 0 | 0 | 0 | 0 | 0 | 0 | 0 | 0 | 0 |
| Barley | 50 | 0 | 0 | 0 | 0 | 0 | 30 | 10 | 10 | 10 | 0 | 0 | 0 | 0 |
| Wild Oats | 100 | 100 | 90 | 95 | 100 | 40 | 100 | 100 | 95 | 100 | 100 | 100 | 80 | 70 |
| | 100 | 50 | 25 | 12.5 | 6.3 | 3.1 | 1.56 | 25 | 12.5 | 6.25 | 3.1 | 1.5 | 0.8 | 0.4 | 0.2 |
| Blackgrass | 100 | 100 | 99 | 100 | 100 | 50 | 50 | 100 | 100 | 99 | 70 | 50 | 30 | 10 | 0 |
| Cheatgrass | 40 | 10 | 0 | 0 | 0 | 0 | 0 | 0 | 0 | 0 | 0 | 0 | 0 | 0 | 0 |
| Green Foxtail | 100 | 100 | 100 | 100 | 100 | 100 | 95 | 100 | 100 | 100 | 100 | 100 | 90 | 90 | 20 |
| Yellow Foxtail | 100 | 100 | 100 | 100 | 100 | 80 | 50 | 100 | 100 | 100 | 80 | 50 | 20 | 0 | 0 |
| | 4-Chloro- (R-Enantiomer) | | | | | | 4-Bromo- (R-Enantiomer) | | | | | | | |
| | 125 | 62.5 | 31.25 | 15.6 | 7.8 | | 250 | 125 | 62.5 | 31.25 | 15.6 | 7.8 | 3.9 | 1.9 |
| Wheat | 60 | 70 | 0 | 0 | 0 | | 100 | 70 | 0 | 0 | 0 | 0 | 0 | 0 |
| Barley | 40 | 0 | 0 | 0 | 0 | | 100 | 90 | 95 | 0 | 0 | 0 | 0 | 0 |
| Wild Oats | 100 | 100 | 100 | 80 | 40 | | 100 | 100 | 100 | 90 | 90 | 80 | 80 | 60 |
| | 25 | 12.5 | 6.3 | 3.2 | 1.6 | 0.8 | 0.4 | 12.5 | 6.3 | 3.1 | 1.5 | 0.8 | 0.4 | 0.2 | 0.1 |
| Blackgrass | 100 | 100 | 95 | 90 | 80 | 40 | 0 | 100 | 100 | 90 | 90 | 60 | 50 | 0 | 0 |
| Cheatgrass | 0 | 0 | 0 | 0 | 0 | 0 | 0 | 0 | 0 | 0 | 0 | 0 | 0 | 50 | 0 |
| Green Foxtail | 100 | 100 | 100 | 100 | 100 | 80 | 0 | 100 | 100 | 100 | 100 | 100 | 100 | 50 | 0 |
| Yellow Foxtail | 100 | 100 | 60 | 40 | 0 | 0 | 0 | 100 | 100 | 100 | 60 | 20 | 0 | 0 | 0 |

EXAMPLE C

Preemergent Activity

In a representative operation, 2-[4-(2-fluoro-4-trifluoromethylphenoxy)phenoxy]propionic acid methyl ester, to be utilized in a series of tests, is dissolved in acetone to one half of the final volume (twice the final concentration) to be used and the acetone solution in each case is admixed with an equal volume of water containing 0.1 percent by weight of Tween-20 surface active material (Tween-20 is a trademark of Atlas Chemical Company). The composition, generally in the nature of an emulsion, was employed to treat separate respective seed beds of sandy loam soil of good nutrient content wherein each seed bed contained separate groups of good viable seeds, each group being of one of a known plant species. The various beds were positioned side by side and exposed to substantially identical conditions of temperature and light. Each bed was maintained so as to prevent any interaction with the test compound in different seed beds. Each seed bed was treated with the composition as a spray employing conventional spraying equipment to deposit a predetermined amount of the compound uniformly throughout the surface of the bed. Another seed bed was treated only with the acetone-Tween-20 water mixture with no chemical added to serve as a control. After treatment, the seed beds were maintained for two weeks under greenhouse conditions conducive for good plant growth and watered as necessary. The specific plant species, dosage and the percent preemergent control obtained are set forth in Table C below. Control refers to the reduction in growth of the test species in the presence of the test chemical relative to the observed growth of the same species in the absence of the test chemical.

TABLE C

Premergence Control of Plant Species (%)
Exhibited by 2-[4-(2-fluoro-4-trifluoromethylphenoxy)phenoxy]propionic
Acid Methyl Ester

| Dosage in Kgs/hectare | Wheat | Barnyard Grass | Crab Grass | Johnson Grass | Wild Oats | Yellow Foxtail |
|---|---|---|---|---|---|---|
| 0.28 | 100 | 100 | 100 | 100 | 100 | 100 |
| 0.114 | 100 | 100 | 100 | 100 | 100 | 100 |
| 0.07 | 90 | 80 | 100 | 90 | 90 | 100 |
| 0.035 | 20 | 70 | 100 | 60 | 20 | 70 |

TABLE C-continued

Premergence Control of Plant Species (%)
Exhibited by 2-[4-(2-fluoro-4-trifluoromethylphenoxy)phenoxy]propionic
Acid Methyl Ester

| Dosage in Kgs/hectare | Wheat | Barnyard Grass | Crab Grass | Johnson Grass | Wild Oats | Yellow Foxtail |
|---|---|---|---|---|---|---|
| 0.018 | 0 | 20 | 40 | 20 | 0 | 20 |

At 0.28 kgs/hectare the compound listed in Table C above was inactive, i.e., no phytotoxic effect, against the seeds of velvet leaf, rape, cotton, soybean, pigweed, jimson weed, sugarbeets and yellow nutsedge.

EXAMPLE D

Preemergent Activity of Racemic (R,S) 2-[4-(4-chloro-2-fluorophenoxy)phenoxy]-propionic Acid Methyl Ester and its R-enantiomer Substantially the same procedures described in Example C were repeated using as the active ingredients
(1) racemic (R,S) 2-[4-(4-chloro-2-fluorophenoxy)-phenoxy]propionic acid methyl ester and
(2) (R) 2-[4-(4-chloro-2-fluorophenoxy)phenoxy]-propionic acid methyl ester.

The results of the preemergence tests are listed in Table D below.

TABLE D

Premergence Control of Plant Species (%)
Exhibited by Racemic (R,S,), and Resolved (R)
2-[4-(4-Chloro-2-fluorophenoxy)phenoxy]propionic
Acid Methyl Ester

| Dosage in Kgs/hectare | Wheat | | Barnyard Grass | | Crabgrass | | Johnson Grass | | Wild Oats | | Yellow Foxtail | |
|---|---|---|---|---|---|---|---|---|---|---|---|---|
| | R,S | R | R,S | R | R,S | R | R,S | R | R,S | R | R,S | R |
| 1.12 | 0 | 20 | 100 | 100 | 100 | 100 | 80 | 98 | 70 | 80 | 95 | 98 |
| 0.56 | 0 | 10 | 100 | 100 | 100 | 100 | 60 | 95 | 50 | 60 | 95 | 95 |
| 0.28 | 0 | 0 | 98 | 98 | 100 | 100 | 0 | 80 | 20 | 0 | 90 | 30 |
| 0.14 | 0 | 0 | 98 | 10 | 100 | 98 | 0 | 0 | 0 | 0 | 10 | 0 |
| 0.07 | 0 | 0 | 40 | 0 | 60 | 70 | 0 | 0 | 0 | 0 | 0 | 0 |

At 1.12 kgs/hectare the compound listed in Table D above were inactive, i.e., no phytotoxic effect, against the seeds of velvet leaf, rape, cotton, soybean, pigweed, jimson weed, sugarbeets and yellow nutsedge.

EXAMPLE E

Employing the procedures set out above in Example C, the following data on preemergent activity of various compounds of the present invention was obtained.

TABLE E

Preemergence Control of Plant Species

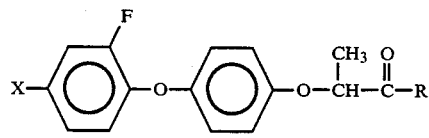

| Compound Tested | | | % Control at Indicated Dosage in kgs/hectare | | | | |
|---|---|---|---|---|---|---|---|
| X | R | Plant Species | 1.12 | .56 | .28 | .14 | .07 |
| Br | —NH—⟨phenyl⟩—CF$_3$ | Wheat | 0 | 0 | 0 | 0 | 0 |
| | | Barnyardgrass | 70 | 50 | 50 | 0 | 0 |
| | | Johnsongrass | 100 | 100 | 20 | 0 | 0 |
| | | Wild Oats | 90 | 90 | 60 | 0 | 0 |
| | | Yellow Foxtail | 100 | 50 | 0 | 0 | 0 |

TABLE E-continued

Preemergence Control of Plant Species

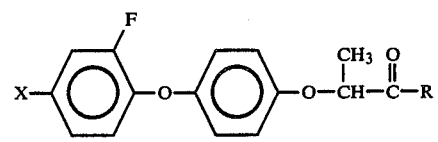

| Compound Tested | | Plant Species | % Control at Indicated Dosage in kgs/hectare | | | | |
|---|---|---|---|---|---|---|---|
| X | R | | 1.12 | .56 | .28 | .14 | .07 |
| Br | Me / —NH—⟨⟩—Cl | Wheat | 40 | 0 | 0 | 0 | 0 |
| | | Barnyardgrass | 100 | 30 | 0 | 0 | 0 |
| | | Johnsongrass | 60 | 0 | 0 | 0 | 0 |
| | | Wild Oats | 90 | 0 | 0 | 0 | 0 |
| | | Yellow Foxtail | 100 | 100 | 70 | 0 | 0 |
| Br | OCH₃ / —NH—⟨⟩ | Wheat | 0 | 0 | 0 | 0 | 0 |
| | | Barnyardgrass | 100 | 100 | 100 | 40 | 0 |
| | | Johnsongrass | 100 | 30 | 30 | 0 | 0 |
| | | Wild Oats | 30 | 40 | 0 | 0 | 0 |
| | | Yellow Foxtail | 100 | 80 | 20 | 0 | 0 |
| Br | —O(CH₂)₇CH₃ | Wheat | 90 | 0 | 0 | 0 | 0 |
| | | Barnyardgrass | 100 | 100 | 100 | 95 | 9 |
| | | Johnsongrass | 100 | 100 | 100 | 0 | 0 |
| | | Wild Oats | 100 | 100 | 100 | 0 | 0 |
| | | Yellow Foxtail | 100 | 90 | 80 | 0 | 0 |
| Br | —O(CH₂)₃CH₃ | Wheat | 30 | 30 | 0 | 0 | 0 |
| | | Barnyardgrass | 100 | 100 | 100 | 70 | 0 |
| | | Johnsongrass | 100 | 100 | 65 | 0 | 0 |
| | | Wild Oats | 100 | 80 | 50 | 0 | 0 |
| | | Yellow Foxtail | 100 | 100 | 95 | 40 | 0 |
| Br | —O(CH₂)₂OC₂H₅ | Wheat | 20 | 0 | 0 | 0 | 0 |
| | | Barnyardgrass | 100 | 100 | 95 | 90 | 0 |
| | | Johnsongrass | 60 | 60 | 0 | 0 | 0 |
| | | Wild Oats | 100 | 100 | 30 | 30 | 0 |
| | | Yellow Foxtail | 100 | 100 | 80 | 0 | 0 |
| Br | —OH | Wheat | 30 | 0 | 0 | 0 | 0 |
| | | Barnyardgrass | 100 | 100 | 100 | 95 | 50 |
| | | Johnsongrass | 100 | 100 | 80 | 60 | 0 |
| | | Wild Oats | 100 | 95 | 90 | 100 | 0 |
| | | Yellow Foxtail | 100 | 100 | 90 | 0 | 0 |
| Br | —OCH₂—C≡CH | Wheat | 0 | 0 | 0 | 0 | 0 |
| | | Barnyardgrass | 100 | 100 | 100 | 20 | 0 |
| | | Johnsongrass | 100 | 100 | 50 | 20 | 0 |
| | | Wild Oats | 70 | 50 | 50 | NT | 0 |
| | | Yellow Foxtail | 100 | 100 | 95 | 60 | 0 |
| Br | —O(CH₂)₂N(CH₃)₂ | Wheat | 0 | 0 | 0 | 0 | 0 |
| | | Barnyardgrass | 100 | 100 | 100 | 100 | 70 |
| | | Johnsongrass | 100 | 95 | 60 | 0 | 0 |
| | | Wild Oats | 99 | 90 | 30 | 30 | 0 |
| | | Yellow Foxtail | 100 | 100 | 0 | 0 | 0 |
| Br | CH₂—CH₂ \ —O—C \ CH₂—CH₂ | Wheat | 80 | 0 | 0 | 0 | 0 |
| | | Barnyardgrass | 100 | 100 | 100 | 50 | 50 |
| | | Johnsongrass | 100 | 100 | 40 | 0 | 0 |
| | | Wild Oats | 100 | 100 | 30 | 0 | 0 |
| | | Yellow Foxtail | 100 | 100 | 100 | 80 | 0 |
| Br | —OCH₂C=CH₂ | Wheat | 70 | 0 | 0 | 0 | 0 |
| | | Barnyardgrass | 100 | 100 | 100 | 100 | 95 |
| | | Johnsongrass | 100 | 90 | 80 | 0 | 0 |
| | | Wild Oats | 70 | 70 | 40 | 0 | 0 |
| | | Yellow Foxtail | 100 | 100 | 90 | 30 | 30 |
| Br | —NH₂ | Wheat | 40 | 90 | 30 | 0 | 0 |
| | | Barnyardgrass | 100 | 100 | 100 | 100 | 20 |
| | | Johnsongrass | 100 | 90 | 30 | 0 | 0 |
| | | Wild Oats | 95 | 50 | 50 | 0 | 0 |
| | | Yellow Foxtail | 100 | 100 | 95 | 90 | 0 |
| Br | CH₃ \ —N \ phenyl | Wheat | 0 | 0 | 0 | 0 | 0 |
| | | Barnyardgrass | 60 | 0 | 0 | 0 | 0 |
| | | Johnsongrass | 80 | 20 | 0 | 0 | 0 |
| | | Wild Oats | 20 | 0 | 0 | 0 | 0 |
| | | Yellow Foxtail | 50 | 50 | 0 | 0 | 0 |

TABLE E-continued
Preemergence Control of Plant Species

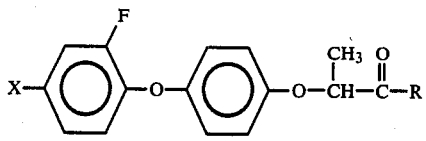

| Compound Tested | | | % Control at Indicated Dosage in kgs/hectare | | | | |
|---|---|---|---|---|---|---|---|
| X | R | Plant Species | 1.12 | .56 | .28 | .14 | .07 |
| Br | —N(H)—CH₂CH=CH₂ | Wheat | 0 | 0 | 0 | 0 | 0 |
| | | Barnyardgrass | 100 | 100 | 100 | 10 | 0 |
| | | Johnsongrass | 100 | 90 | 50 | 30 | 0 |
| | | Wild Oats | 90 | 80 | 90 | 90 | 80 |
| | | Yellow Foxtail | 100 | 90 | 30 | 0 | 0 |
| I | —OCH₃ | Wheat | 20 | 20 | 0 | 0 | 0 |
| | | Barnyardgrass | 100 | 97 | 100 | 50 | NT |
| | | Johnsongrass | 100 | 99 | 60 | 0 | 0 |
| | | Wild Oats | 99 | 95 | 0 | 0 | 0 |
| | | Yellow Foxtail | 100 | 100 | 20 | 0 | 0 |

NT = Not Tested

EXAMPLE F

To further define the selective postemergence herbicidal characteristics of compounds of the present invention, chemicals were applied to additional species of grasses as listed in Table F. Chemicals evaluated were 2-[4-(4-bromo-2-fluorophenoxy)phenoxy]propionic acid methyl ester and its R isomer. Treatment conditions were similar to those described in Example A except that chemicals were delivered through a track sprayer set to deliver the appropriate dosages in 280.6 L/hectare of water containing 0.1% Tween-20 surfactant. Results are presented in Table F.

TABLE F

| | Percent Control at Indicated Rate (kgs/hectare) | | | | | | | | | |
|---|---|---|---|---|---|---|---|---|---|---|
| | Racemic Mixture | | | | | | | | | |
| | 0.56 | 0.28 | 0.14 | 0.07 | 0.035 | 0.018 | 0.009 | 0.0045 | 0.0023 | 0.0011 |
| Barley | 50 | 20 | 10 | 0 | 0 | 0 | 0 | 0 | 0 | 0 |
| Wheat | 50 | 40 | 10 | 0 | 0 | 0 | 0 | 0 | 0 | 0 |
| Annual Rye | 100 | 100 | 100 | 100 | 40 | NT | 20 | 0 | 0 | 0 |
| Wild Oats | 100 | 90 | 70 | 40 | 40 | NT | 0 | 0 | 0 | 0 |
| Goosegrass | 100 | 100 | 100 | 100 | 80 | NT | 20 | 30 | 0 | 0 |
| Crabgrass | 100 | 100 | 100 | 100 | 100 | NT | 50 | 50 | 0 | 0 |
| Annual Bluegrass | 0 | 0 | 0 | 0 | 0 | 0 | 0 | 0 | 0 | 0 |
| Wild Proso Millet | 100 | 100 | 100 | 100 | 100 | NT | 80 | 70 | 20 | 20 |
| Green Foxtail | 100 | 100 | 100 | 100 | 100 | NT | 90 | 90 | 20 | 0 |
| Barnyardgrass | 100 | 100 | 100 | 100 | 100 | NT | 100 | 100 | 70 | 40 |
| Johnsongrass | 80 | 30 | 20 | 0 | 0 | NT | 0 | 0 | 0 | 0 |
| Yellow Foxtail | 100 | 100 | 100 | 100 | 80 | NT | 40 | 0 | 0 | 0 |
| Red Top | 100 | 100 | 90 | 80 | 50 | NT | 20 | 0 | 0 | 0 |
| Sprangletop | 100 | 100 | 100 | NT | 100 | NT | 100 | 95 | 20 | 0 |
| Fall Panicum | 100 | 100 | NT | NT | 100 | NT | 80 | 50 | 20 | 0 |
| Giant Foxtail | 100 | 100 | 100 | NT | 100 | NT | 100 | 100 | 100 | 100 |
| Tall Fescue | 95 | 95 | 90 | NT | 60 | NT | 20 | 20 | 10 | 0 |
| Canarygrass | 100 | 100 | 100 | 100 | 50 | NT | 0 | 0 | 0 | 0 |
| Broadleaf Signalgrass | 100 | 100 | 100 | 100 | 100 | NT | 100 | 80 | 90 | 70 |
| Cheatgrass | 20 | 0 | 0 | 0 | 0 | 0 | 0 | 0 | 0 | 0 |
| Bermudagrass | 100 | 100 | 90 | 95 | 90 | NT | 20 | 0 | 0 | 0 |
| Orchardgrass | 90 | 90 | 90 | 80 | 0 | NT | 0 | 0 | 0 | 0 |
| Downey Brome | 0 | 0 | 0 | 0 | 0 | 0 | 0 | 0 | 0 | 0 |
| Blackgrass | 100 | 100 | 100 | 100 | 100 | NT | 100 | 50 | 50 | 30 |
| | R Resolved Isomer Form | | | | | | | | | |
| | 0.28 | 0.14 | 0.07 | 0.035 | 0.018 | 0.009 | 0.0045 | 0.0023 | 0.0011 | 0.00055 |
| Barley | 0 | 0 | 0 | 0 | 0 | 0 | 0 | 0 | 0 | 0 |
| Wheat | 0 | 0 | 0 | 0 | 0 | 0 | 0 | 0 | 0 | 0 |
| Annual Rye | 90 | 90 | 70 | 60 | 30 | 20 | 0 | 0 | 0 | 0 |
| Wild Oats | 95 | 70 | 70 | 40 | 20 | 20 | 0 | 0 | 0 | 0 |
| Goosegrass | 80 | 80 | 70 | 70 | 50 | 70 | 20 | 0 | 0 | 0 |
| Crabgrass | 100 | 100 | 100 | 70 | 90 | 90 | 50 | 0 | 0 | 0 |
| Annual Bluegrass | 0 | 0 | 0 | 0 | 0 | 0 | 0 | 0 | 0 | 0 |
| Wild Proso Millet | 100 | 100 | 100 | 100 | 100 | 95 | 100 | 80 | 30 | 30 |
| Green Foxtail | 100 | 100 | 100 | 100 | 100 | 95 | 95 | 90 | 70 | 30 |
| Barnyardgrass | 100 | 100 | 100 | 100 | 100 | 100 | 100 | 100 | 80 | 90 |
| Johnsongrass | 70 | 40 | 20 | 0 | 0 | 0 | 0 | 0 | 0 | 0 |
| Yellow Foxtail | 100 | 100 | 100 | 100 | 90 | 50 | 20 | 20 | 0 | 0 |
| Red Top | 90 | 90 | 90 | 30 | 0 | 0 | 0 | 0 | 0 | 0 |
| Sprangletop | 100 | 100 | 100 | 100 | 100 | 100 | 100 | 100 | 20 | 0 |

TABLE F-continued

| | Percent Control at Indicated Rate (kgs/hectare) | | | | | | | | | |
|---|---|---|---|---|---|---|---|---|---|---|
| Fall Panicum | 100 | 100 | 100 | 100 | 100 | 80 | 80 | 50 | 30 | 20 |
| Giant Foxtail | 100 | 100 | 100 | 100 | 100 | 100 | 100 | 100 | 100 | 80 |
| Tall Fescue | 90 | 90 | 90 | 80 | 70 | 50 | 20 | 0 | 0 | 0 |
| Canarygrass | 100 | 100 | 100 | 100 | 0 | 0 | 0 | 0 | 0 | 0 |
| Broadleaf Signalgrass | 100 | 100 | 100 | 100 | 100 | 95 | 90 | 50 | 50 | 50 |
| Cheatgrass | 0 | 0 | 0 | 0 | 0 | 0 | 0 | 0 | 0 | 0 |
| Bermudagrass | 95 | 90 | 90 | 90 | 60 | 30 | 20 | 0 | 0 | 0 |
| Orchardgrass | 50 | 0 | 0 | 0 | 0 | 0 | 0 | 0 | 0 | 0 |
| Downey Brome | 0 | 0 | 0 | 0 | 0 | 0 | 0 | 0 | 0 | 0 |
| Blackgrass | 100 | 100 | 100 | 100 | 100 | 80 | 60 | 60 | 60 | 50 |

The compounds of the present invention contain an optically active center as shown in Formula (I) (2 position of the propanoic acid) and can exist in optically active steroisomeric forms such as the dextrorotatory and levorotatory forms of each of the above configurations. The various mixtures and racemates, i.e., enantiomers, isomers are within the scope of the present invention.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

What is claimed is:

1. A compound of the formula

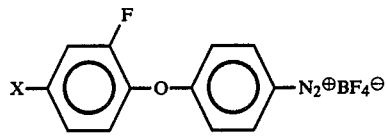

wherein X represents —Cl, —$CF_3$, —I, —Br, F, —$OCF_3$, —$CF_2Cl$, —$CF_2H$ or —$OCF_2CCl_2H$.

2. The compound of claim 1 wherein X represents —Cl.

3. The compound of claim 1 wherein X represents —Br.

4. The compound of claim 1 wherein X represents —$CF_3$.

5. A compound of the formula

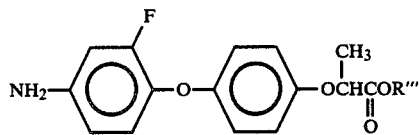

where R''' is $C_1$–$C_8$ alkyl.

6. Compound of claim 5 where R''' is methyl.

* * * * *

UNITED STATES PATENT AND TRADEMARK OFFICE
CERTIFICATE OF CORRECTION

PATENT NO. : 4,642,338

DATED : February 10, 1987

INVENTOR(S) : Richard B. Rogers and B. Clifford Gerwick III

It is certified that error appears in the above-identified patent and that said Letters Patent is hereby corrected as shown below:

Col. 5, line 11, "thio" should read -- thiol --.

Col. 5, lines 25-28, the formula should read

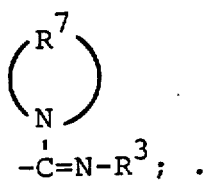

Col. 7, line 39, "trifluoroacetate" should read -- trifluoroacetic --. (second occurrence)

Col. 7, line 40, "procedure" should read -- procedures --.

Col. 9, line 39, "1∝4" should read -- 1-4 --.

Col. 15, line 64, "tetrafluorobate" should read -- tetrafluoroborate --.

Col. 17, line 51, "powered" should read -- powdered --.

UNITED STATES PATENT AND TRADEMARK OFFICE
CERTIFICATE OF CORRECTION

PATENT NO. : 4,642,338

DATED : February 10, 1987

INVENTOR(S) : Richard B. Rogers and B. Clifford Gerwick III

It is certified that error appears in the above-identified patent and that said Letters Patent is hereby corrected as shown below:

Col. 20, line 33, "rionate" should read -- ionate --.

Col. 24, line 6, "proponamide" should read -- propionamide --.

Col. 24, line 20, "butylamide" should read -- butylamine --.

Col. 25, line 56, "01 mol" should read -- 0.01 mol --.

Col. 28, line 28, "mxiture" should read -- mixture --.

Col. 29, line 24, that portion of the formula should read

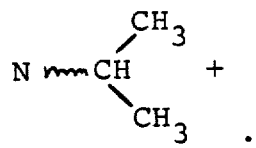

Col. 29, line 35, that portion of the formula should read

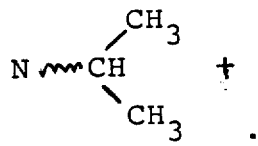

UNITED STATES PATENT AND TRADEMARK OFFICE
CERTIFICATE OF CORRECTION

PATENT NO. : 4,642,338

DATED : February 10, 1987

INVENTOR(S) : Richard B. Rogers and B. Clifford Gerwick III

It is certified that error appears in the above-identified patent and that said Letters Patent is hereby corrected as shown below:

Col. 30, line 29, "proprionate" should read -- propionate --.

Col. 30, line 36, "was" should be deleted.

Col. 31, line 7, "diazonnium" should read -- diazonium --.

Col. 31, line 11, "diazonnium" should read -- diazonium --.

Col. 31, line 13, "at" should read -- to --.

Col. 33, line 30, "diatomeaceous" should read -- diatomaceous --.

Col. 35, line 12, "25 ppm" should read -- 125 ppm --.

Col. 38, the footnote of Table D, "compound" should read -- compounds --.

Signed and Sealed this

Nineteenth Day of September, 1989

Attest:

DONALD J. QUIGG

Attesting Officer

Commissioner of Patents and Trademarks